US008226724B2

(12) United States Patent
Doty

(10) Patent No.: US 8,226,724 B2
(45) Date of Patent: Jul. 24, 2012

(54) INTERVERTEBRAL SPINAL DISC PROSTHESIS

(76) Inventor: Keith L. Doty, Gainesville, FL (US)

( * ) Notice: Subject to any disclaimer, the term of this patent is extended or adjusted under 35 U.S.C. 154(b) by 471 days.

(21) Appl. No.: 12/487,207

(22) Filed: Jun. 18, 2009

(65) Prior Publication Data

US 2010/0324688 A1 Dec. 23, 2010

(51) Int. Cl.
A61F 2/44 (2006.01)
(52) U.S. Cl. ................. 623/17.16; 623/17.11
(58) Field of Classification Search ..... 623/17.11–17.16
See application file for complete search history.

(56) References Cited

U.S. PATENT DOCUMENTS

| 4,714,469 A | 12/1987 | Kenna |
| 4,759,766 A | 7/1988 | Buettner-Janz et al. |
| 4,759,769 A | 7/1988 | Hedman et al. |
| 4,846,840 A | 7/1989 | Leclercq et al. |
| 4,863,476 A | 9/1989 | Shepperd |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,997,432 A | 3/1991 | Keller |
| 5,002,576 A | 3/1991 | Fuhrmann et al. |
| 5,024,670 A | 6/1991 | Smith et al. |
| 5,037,438 A | 8/1991 | Davidson |
| 5,047,055 A | 9/1991 | Bao et al. |
| 5,071,437 A | 12/1991 | Steffee |
| 5,080,675 A | 1/1992 | Lawes et al. |
| 5,258,031 A | 11/1993 | Salib et al. |
| 5,258,043 A | 11/1993 | Stone |
| 5,306,307 A | 4/1994 | Senter et al. |
| 5,306,308 A | 4/1994 | Gorss et al. |
| 5,306,309 A | 4/1994 | Wagner et al. |
| 5,306,412 A | 4/1994 | Whitehouse et al. |
| 5,314,477 A | 5/1994 | Marnay |
| 5,314,478 A | 5/1994 | Oka et al. |
| 5,320,644 A | 6/1994 | Baumgartner |
| 5,401,269 A | 3/1995 | Buttner-Janz et al. |
| 5,415,704 A | 5/1995 | Davidson |

(Continued)

FOREIGN PATENT DOCUMENTS

EP 1 572 038 9/2005

(Continued)

OTHER PUBLICATIONS

Bao et al., "Artificial Disc Technology," *Neurosurg Focus*, American Association of Neurological Surgeons, Oct. 2000, pp. 1-7, vol. 9, No. 4.

(Continued)

*Primary Examiner* — Eduardo C Robert
*Assistant Examiner* — Nicholas Plionis
(74) *Attorney, Agent, or Firm* — Saliwanchik Lloyd & Eisenschenk

(57) ABSTRACT

The subject invention provides a modular six-degrees-of-freedom spatial mechanism for spinal disc prosthesis, with three rotational and three translational degrees-of-freedom. The prosthesis anchors to the superior and inferior vertebrae of an FSU and maintains mechanical linkage between those vertebrae for all normal motions and positions of the FSU. The prosthetic disc uses a novel, multi-curvate "ball-and-socket" joint with joint limits on all three rotational axes integrated into the design. A planar joint can further provide two, orthogonal linear degrees of freedom. Resilient spring elements, self-adjusting, in position and orientation, in conjunction with a double-layered, fiber and ring reinforced boot and toroidal belt, and a unique hydraulic damping system using dual segmented-walls can accommodate dynamic and static forces and sudden shocks on the FSU.

114 Claims, 20 Drawing Sheets

U.S. PATENT DOCUMENTS

| | | | |
|---|---|---|---|
| 5,425,773 A | 6/1995 | Boyd et al. |
| 5,458,642 A | 10/1995 | Beer et al. |
| 5,674,296 A | 10/1997 | Bryan et al. |
| 5,676,701 A | 10/1997 | Yuan et al. |
| 5,782,832 A | 7/1998 | Larsen et al. |
| 5,827,328 A | 10/1998 | Buttermann |
| 5,865,846 A | 2/1999 | Bryan et al. |
| 6,001,130 A | 12/1999 | Bryan et al. |
| 6,019,792 A | 2/2000 | Cauthen |
| 6,156,067 A | 12/2000 | Bryan et al. |
| 6,179,874 B1 | 1/2001 | Cauthen |
| 6,315,797 B1 | 11/2001 | Middleton |
| 6,368,350 B1 | 4/2002 | Erickson et al. |
| 6,395,032 B1 | 5/2002 | Gauchet |
| 6,419,706 B1 | 7/2002 | Graf |
| 6,626,943 B2 | 9/2003 | Eberlein et al. |
| 6,645,248 B2 | 11/2003 | Casutt |
| 6,656,224 B2 | 12/2003 | Middleton |
| 6,669,732 B2 | 12/2003 | Serhan et al. |
| 6,682,562 B2 | 1/2004 | Viart et al. |
| 6,726,721 B2 | 4/2004 | Stoy et al. |
| 6,733,532 B1 | 5/2004 | Gauchet et al. |
| 6,736,850 B2 | 5/2004 | Davis |
| 6,740,118 B2 | 5/2004 | Eisermann et al. |
| 6,749,635 B1 | 6/2004 | Bryan |
| 6,770,095 B2 | 8/2004 | Grinberg et al. |
| 6,802,867 B2 | 10/2004 | Manasas et al. |
| 6,833,006 B2 | 12/2004 | Foley et al. |
| 6,960,232 B2 | 11/2005 | Lyons et al. |
| 6,964,686 B2 | 11/2005 | Gordon |
| 6,966,929 B2 | 11/2005 | Mitchell |
| 6,981,989 B1 | 1/2006 | Fleischmann et al. |
| 6,989,032 B2 | 1/2006 | Errico et al. |
| 6,994,727 B2 | 2/2006 | Khandkar et al. |
| 7,001,433 B2 | 2/2006 | Songer et al. |
| 7,011,685 B2 | 3/2006 | Arnin et al. |
| 7,014,658 B2 | 3/2006 | Ralph et al. |
| 7,022,138 B2 | 4/2006 | Mashburn |
| 7,022,139 B2 | 4/2006 | Errico et al. |
| 7,044,969 B2 | 5/2006 | Errico et al. |
| 7,048,763 B2 | 5/2006 | Ralph et al. |
| 7,060,100 B2 | 6/2006 | Ferree et al. |
| 7,066,960 B1 | 6/2006 | Dickman |
| 7,101,400 B2 | 9/2006 | Thramann et al. |
| 7,122,055 B2 | 10/2006 | Ralph et al. |
| 7,156,876 B2 | 1/2007 | Moumene et al. |
| 7,163,559 B2 | 1/2007 | Errico et al. |
| 7,186,268 B2 | 3/2007 | Errico et al. |
| 7,195,644 B2 | 3/2007 | Diaz et al. |
| 7,198,643 B2 | 4/2007 | Zubok et al. |
| 7,208,014 B2 | 4/2007 | Ralph et al. |
| 7,214,244 B2 | 5/2007 | Zubok et al. |
| 7,223,290 B2 | 5/2007 | Errico et al. |
| 7,258,699 B2 | 8/2007 | Errico et al. |
| 7,261,739 B2 | 8/2007 | Ralph et al. |
| 7,270,680 B2 | 9/2007 | Ralph et al. |
| 7,270,681 B2 | 9/2007 | Cauthen |
| 7,273,496 B2 | 9/2007 | Mitchell |
| 7,276,082 B2 | 10/2007 | Zdeblick et al. |
| 7,291,171 B2 | 11/2007 | Ferree et al. |
| 7,314,487 B2 | 1/2008 | Ralph et al. |
| 7,316,714 B2 | 1/2008 | Gordon et al. |
| 7,331,994 B2 | 2/2008 | Gordon et al. |
| 7,331,995 B2 | 2/2008 | Eisermann et al. |
| 7,338,525 B2 | 3/2008 | Ferree |
| 7,361,192 B2 | 4/2008 | Doty |
| 2002/0111681 A1 | 8/2002 | Ralph et al. |
| 2003/0014110 A1 | 1/2003 | Ralph et al. |
| 2003/0014112 A1 | 1/2003 | Ralph et al. |
| 2004/0167626 A1 | 8/2004 | Geremakis et al. |
| 2004/0260396 A1 | 12/2004 | Ferree |
| 2005/0015152 A1 | 1/2005 | Sweeney |
| 2005/0192670 A1 | 9/2005 | Zubok |
| 2005/0234555 A1 | 10/2005 | Sutton |
| 2005/0240270 A1 | 10/2005 | Zubok |
| 2005/0273169 A1 | 12/2005 | Purcell |
| 2006/0036324 A1 | 2/2006 | Sachs et al. |
| 2006/0136062 A1 | 6/2006 | Dinello et al. |
| 2006/0235525 A1 | 10/2006 | Gil et al. |
| 2006/0235527 A1 | 10/2006 | Buettner-Janz et al. |
| 2006/0235529 A1 | 10/2006 | Ralph |
| 2006/0241767 A1 | 10/2006 | Doty |
| 2007/0067038 A1 | 3/2007 | Studer et al. |
| 2007/0073403 A1 | 3/2007 | Lombardo et al. |
| 2007/0150062 A1 | 6/2007 | Zubok |
| 2008/0015699 A1 | 1/2008 | Voydeville |
| 2008/0021557 A1 | 1/2008 | Trieu |
| 2008/0027547 A1 | 1/2008 | Yu |
| 2008/0058940 A1 | 3/2008 | Wu |
| 2008/0065211 A1 | 3/2008 | Albert |
| 2008/0077242 A1 | 3/2008 | Reo |
| 2008/0077244 A1 | 3/2008 | Robinson |
| 2008/0077246 A1 | 3/2008 | Fehling |
| 2010/0070033 A1 | 3/2010 | Doty |

FOREIGN PATENT DOCUMENTS

| | | |
|---|---|---|
| WO | WO 00-53127 | 9/2000 |
| WO | WO 2007-065443 | 6/2007 |
| WO | WO 2007/076194 A2 | 7/2007 |
| WO | WO 2007/076194 A3 | 7/2007 |

OTHER PUBLICATIONS

Bao et al., "The artificial disc: theory, design and materials," *Biomaterials*, 1996, pp. 1157-1167, vol. 17, No. 12.

Bogduk, N. et al., "Biomechanics of the cervical spine. I: Normal kinematics," *Clinical Biomechanics*, 2000, pp. 633-648, vol. 15.

Bogduk et al., "A biological basis for instantaneous centers of rotation of the vertebral column", *Proc. Instn. Mech. Engrs.*, 1995, pp. 177-183, vol. 209.

Bogduk et al., "*Clinicial Anatomy of the Lumbar Spine*", ISBN 0-443-03505-9, 1987, Churchill-Livingstone Melbourne Edinburgh London New York.

Büttner-Jantz, et al., *The Artificial Disc*, ISBN 3-540-41779-6, 2003, Springer-Verlag, Berlin Heidelberg New York.

van Mameren et al., "Cervical Spine Motion in the Sagittal Plane II: Position of Segmental Averaged Instantaneous Centers of Rotation—A Cineradiographic Study," *Spine*, 1992, pp. 467-474, vol. 17, No. 5.

Mow et al., "*Basic Orthopaedic Biomechanics*", Lippincott-Raven Pub., N.Y., 2$^{nd}$ Edition, 1997.

Panjabi, M. "Instantaneous Center of Rotation and Instability of the Cervical Spine: A Clinical Study," *Spine*, 1997, pp. 647-648, vol. 22, No. 6.

Panjabi et al., "Articular Facets of the Human Spine: Quantitative Three-Dimensional Anatomy," *Spine*, 1993, pp. 1298-1310, vol. 18, No. 10.

Yoganandan N. et al., "Chapter 5—Biomechanics of the Cervival Spine," *Principles of Spinal Surgery*, 1996, pp. 69-83.

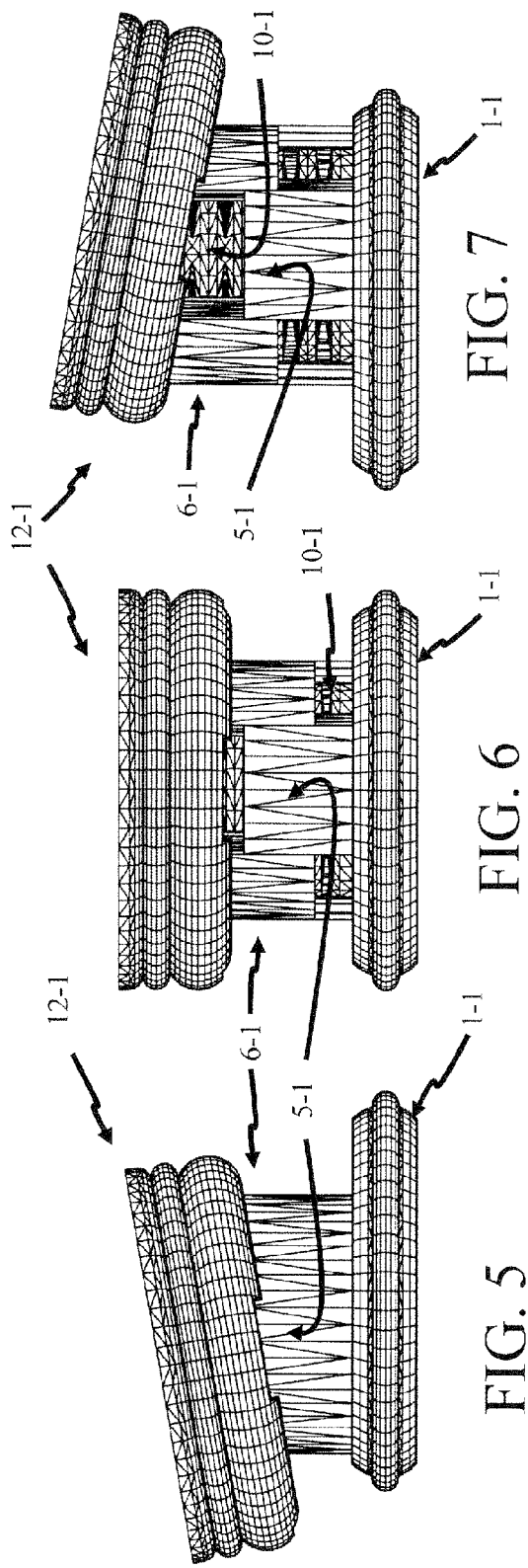

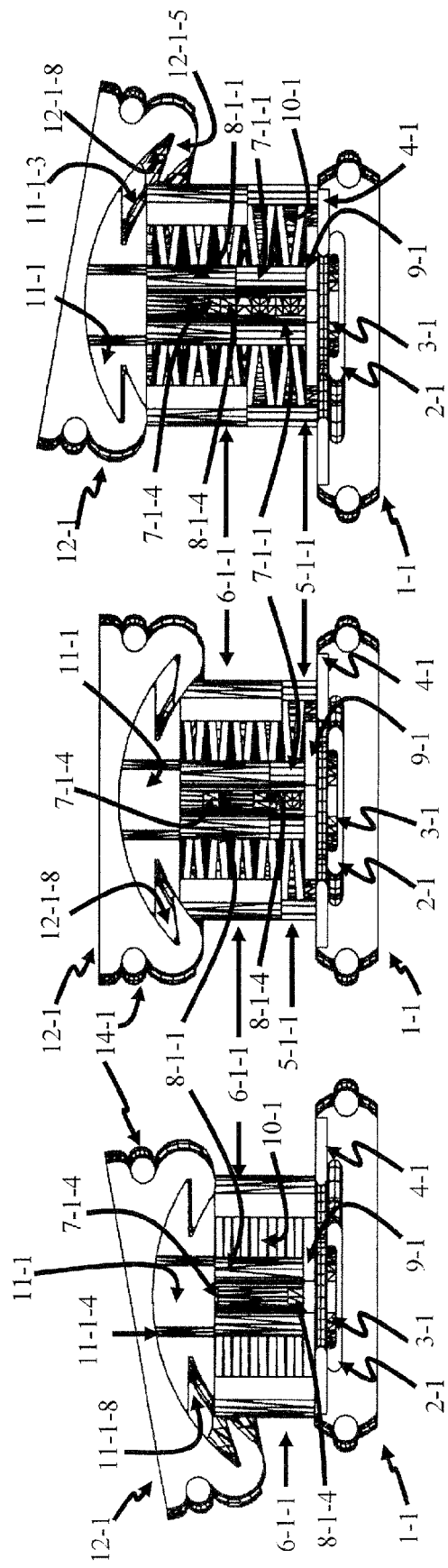

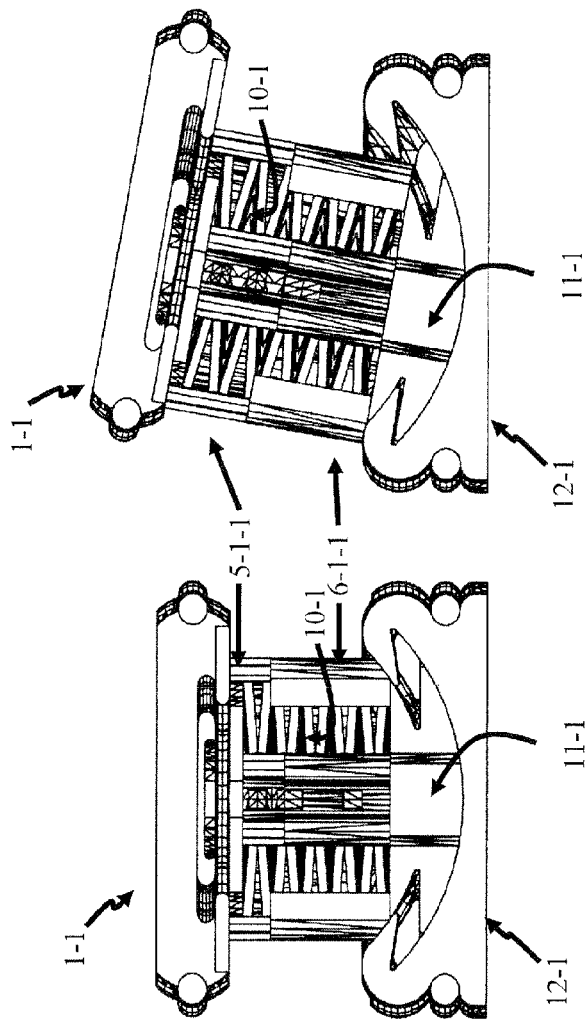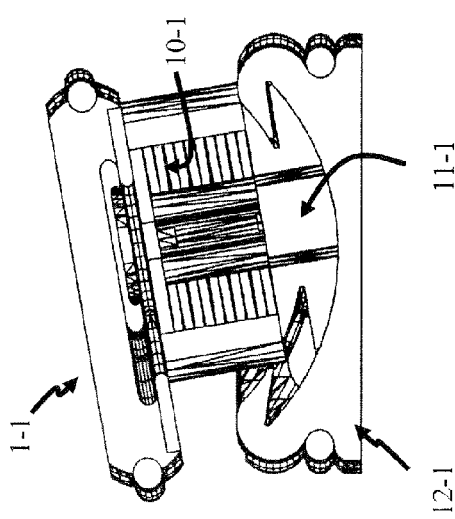
Fig. 35  Fig. 36  Fig. 37

INTERVERTEBRAL SPINAL DISC PROSTHESIS

BACKGROUND OF INVENTION

Spinal disc herniation, a common ailment, often induces pain, as well as neurologically and physiologically debilitating processes for which relief becomes paramount. If conservative treatments fail, the more drastic measures of discectomies and spinal fusion may be indicated. The latter treatment, while providing short term relief, often leads to excessive forces on facet joints adjacent to the fusion and creates further problems over time. Drastic treatments are usually unable to restore normal disc function. The loss of disc function has led to a number of disc prosthesis that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474). This motion varies widely between functional spinal units on an individual spine and between individuals and can depend on age, time-of-day, and the general health and condition of the intervertebral discs, facet joints and other components of the FSU and spine. A moving IAR means that the superior vertebra both rotates and translates while moving with respect to the inferior vertebra of an FSU. Natural spinal motions place severe requirements on the design of a prosthetic disc; simple rotational joints are not able meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

Researchers have attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", Clinical Biomechanics, Elsevier, 15 (2000) 633-648; and Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474), this restricted motion does not correspond to the natural motion of the vertebrae, either for sagittal plane motion or for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability and excessive facet loading.

As a further elaboration on the many ball-and-socket configurations, consider Salib et. al. (U.S. Pat. No. 5,258,031) as an example of previous efforts to address this problem. The Salib et al. ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit.

Currently known devices appear to have similar motion and instability limitations, such as the rocker arm device disclosed by Cauthen (U.S. Pat. Nos. 6,019,792; 6,179,874; 7,270,681), the freely moving sliding disc cores found in the Bryan et al. patents (U.S. Pat. Nos. 5,674,296; 5,865,846; 6,001,130; and 6,156,067) and the SB Charité™ prosthesis, as described by Búttner-Jantz K., Hochschuler S. H., McAfee P. C. (Eds), The Artificial Disc, ISBN 3-540-41779-6 Springer-Verlag, Berlin Heidelberg New York, 2003; and U.S. Pat. No. 5,401,269; and Buettner-Jantz et al. U.S. Pat. No. 4,759,766). In addition, the sliding disc core devices of the Bryan et al. and SB Charité™ devices do not permit natural motion of the joint for any fixed shape of the core.

With the above described prosthetic devices, when the FSU extends, the prosthesis's sliding core, in some cases, generates unnatural constraining forces on the FSU by restricting closure of the posterior intervertebral gap in the FSU. Further, the core does not mechanically link the upper and lower plates of the prosthesis and is unable to maintain the intervertebral gap throughout the range of motion. Such conditions can contribute to prosthetic disc spondylolisthesis. In general, unconstrained or over-constrained relative motion between the two vertebral plates in a prosthetic disc can contribute to FSU instability over time.

Current prosthetic disc technology appears to be limited in static and dynamic load handling capability. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the intervertebral gap requirements during motion, and may likely generate excessive reaction forces on the spine during flexion, forces that can potentially produce extra stress on facet joints and effect mobility.

More recent attempts to provide dynamic and static loading capability is taught in the series of patents by Ralph et al (U.S. Pat. Nos. 6,645,249, 6,863,688, 6,863,688, 7,014,658, 7,048,763, 7,122,055, 7,208,014, 7,261,739, 7,270,680, 7,314,487) wherein the force restoring mechanism begins with a multi-pronged domed spring between two plates and ends with a wave-washer as the force restoring element. The multi-pronged domed spring employs a ball-and-socket arrangement on the upper plate and allows relative rotations between the spring-lower plate and the upper plate. This arrangement, during normal FSU operation, places moments of force on the spring that tend to distort the spring and place high stresses on the set screws holding the spring down. The effects of force moments on the prongs and the dome spring is mitigated by later designs where various modifications of the spring element, as for example the spiral Belleville washer in U.S. Pat. No. 7,270,680, provides the spring more resilience to moments of force. As taught in these patents, the motion of the upper plate is limited to compression and rotation. Lateral and sagittal translations are not accommodated and so general motion in the FSU is not enabled by the device.

The work of Errico et al (U.S. Pat. Nos. 6,989,032, 7,022,139, 7,044,969, 7,163,559, 7,186,268, 7,223,290, and 7,258,699) elaborates on the mechanical design of the patents of Ralph et al. A specially designed Belleville type washer provides a restoring force to compressions. Rotations of the superior plate of the device in a fixed ball-and-socket arrangement transfers moments of force about the washer central axis to a rigid structure. It is notable that the instruction in these designs specifically proscribes lateral motions (sagittal and lateral translation). Errico et al employ a taper attached to the ball to limit rotation angles.

Another approach to incorporate dynamic and static force response is taught by Gauchet (U.S. Pat. Nos. 6,395,032, 6,527,804, 6,579,320, 6,582,466, 6,582,468, and 6,733,532) wherein a hydraulic system provides shock absorption by means of a cushion between two plates contained within sealed flexible titanium bellows. Gauchet suggests the bellows can be designed to accommodate lateral forces and axial rotation that is permitted by the cushion, which, to allow sliding motion, is not attached to at least one plate. The titanium bellows can accommodate some axial rotations, but do not seem suitable for other rotations, which can cause excessive stresses on the bellows. A cushion internal to the cylinder, being flexible and not attached to at least one plate, can accommodate any rotation (U.S. Pat. Nos. 6,582,466 and 6,733,532).

Fleishman et al in U.S. Pat. Nos. 6,375,682 and 6,981,989 utilize hydraulic action coupled with a flexible bellows to mitigate sudden forces. The bellows concept is similar to that of Gauchet.

Eberlein et al (U.S. Pat. No. 6,626,943) utilizes a fiber ring to enclose a flexible element. The forces and moments of force are absorbed by the ring and the flexible element. The device taught in this invention uses a boot in much the same manner as Eberlein's fiber ring. Other inventions teach this concept as well, namely, Casutt in U.S. Pat. No. 6,645,248. Diaz et al (U.S. Pat. No. 7,195,644) also uses a membrane and enclosed cushioning material in their ball and dual socket joint design.

Middleton suggests a variety of machined springs as the central component of a disc prosthesis in U.S. Pat. Nos. 6,136,031, 6,296,664, 6,315,797, and 6,656,224. The spring is notched to allow static and dynamic response primarily in the axial direction of the spring. But, lateral and sagittal translations and general rotations appear to be problematic in these designs. The ability of such springs to tolerate off-axis compression forces may also be problematic.

Gordon instructs deforming a machined spring as the principle separating and force management component (U.S. Pat. Nos. 6,579,321, 6,964,686, and 7,331,994). In U.S. Pat. No. 7,316,714 the emphasis is on posterior insertion of a disc prosthesis that can provide appropriate motion. However, this latter design does not appear to accommodate for static and dynamic loading and there appears to be no accommodation for lateral and sagittal translations.

Zubok instructs in U.S. Pat. No. 6,972,038 (Column 3; Line 35) that " . . . the present invention contemplates that with regard to the cervical anatomy, a device that maintains a center of rotation, moving or otherwise, within the disc space is inappropriate and fails to properly support healthy motion."

This statement may be true as long as translations within the prosthesis mechanism do not adequately compensate for the total motion induced by an IAR outside of the disc space.

Several approaches by Ferree (U.S. Pat. Nos. 6,419,704, 6,706,068, 6,875,235, 7,048,764, 7,060,100, 7,201,774, 7,201,776, 7,235,102, 7,267,688, 7,291,171, and 7,338,525) primarily instruct how to cushion a prosthetic FSU in various ways. An exception is U.S. Pat. No. 6,706,068, which describes a design to perform certain kinematic motion of a disc prosthesis without dynamic or static cushioning support, and U.S. Pat. No. 7,338,525, which instructs on anchoring a disc prosthesis.

Aebi incorporates what essentially amounts to a hook joint (orthogonal revolute joints) in EP1572038B1 as the means for realizing motion. While the Aebi arrangement of revolute joints does allow for sagittal and lateral rotations, it does not engage in the remaining four degrees of freedom in three-space, namely, sagittal, lateral, and axial translations along with axial rotations. Mitchell (U.S. Pat. No. 7,273,496B2) uses two revolute joints by means of orthogonal cylinders placed on top of each other and embedded as a crossbar element between vertebral plates with cavities for accepting the crossbar. This device has the limitations of motion similar to the Aebi device and the further limitation of not kinematically linking the two plates together with the crossbar.

Khandkar (U.S. Pat. No. 6,994,727 B2) provides two orthogonal convex curvate bearing structures, with offset cylindrical radii of curvature, placed between the vertebral plates. An insert, with orthogonal, variable-curvature concave bearing surfaces, is placed between, and generally conforms to, the orthogonal convex bearings on the vertebral plates. This arrangement of bearings allows sagittal, lateral, and axial rotations of various ranges, dictated by the curvate bearing structures and the insert. The variable curvate surfaces allows some lateral and sagittal translations with FSU distractions, utilizing normal spinal forces to resist the distraction and, hence, the motion. There is no control on the forces involved, so this method could lead to possible stress on other spinal joints. The inserted device is not kinematically chained to the rest of the device and can possibly be spit out. Although, as instructed, the device is self-correcting within a limited range, tending towards a stable equilibrium established for the device in normal position. The variable curvatures result, typically, in line-contact bearing manifolds that will wear the surfaces, possibly causing changes in the performance and characteristic motion of the device.

DiNello (US Publication No. 2006/0136062A1) instructs on how to adjust height and angulation of a motion disc after implantation.

With respect to the lower vertebra in an FSU, all possible, natural loci of motion of any four non-planar, non-collinear points located in the superior vertebra define the natural workspace of an FSU. This workspace varies from one FSU to another on the spine, creating considerable spinal disc prosthesis design problems.

The spinal disc prosthesis of the subject invention provides a general motion spatial mechanism that solves the natural motion problem for disc prosthesis and offers a scalable mechanism for disc replacement without loss of general motion capabilities in the FSU.

BRIEF SUMMARY

The subject invention provides a spinal disc prosthesis capable of providing spatial movement with up to 6 degrees of freedom. Advantageously, the device of the subject invention can facilitate normal motion by allowing independent sagittal, lateral, and axial vertebral displacements and rotations when utilized in the spine of a patient.

In one embodiment, the modular spinal disc prosthesis of the subject invention comprises superior and inferior vertebral plates, that secure a replaceable six-degrees of freedom (6-DOF) modular prosthetic disc mechanism (linkage). The devices of the subject invention can achieve up to 6 degrees of freedom, including up to 3 independent rotational degrees of freedom and up to 3 independent linear degrees of freedom, such that the device of the subject invention facilitates sagittal, lateral, and axial vertebral displacements and rotations when utilized in the spine of a patient. The modular prosthetic disc mechanism of the subject invention can utilize a multi-curvate ball-and-socket type joint coupled with a central, compressible and extendible hydraulic cylinder attached orthogonally to a planar bearing for general positioning and orienting of the superior vertebra with respect to the inferior vertebra of a Functional Spinal Unit (FSU). In a particular embodiment the multi-curvate surfaces are generally spherical with a common center.

In one embodiment, the interior mechanisms of the invention kinematically connect a superior and inferior vertebral plate by means of mechanically interlocked and inseparable joint elements. The planar bearing permits sagittal and lateral displacements within the inferior vertebral plate, but cannot move in the axial direction and, thus, cannot separate from the inferior vertebral plate. The central hydraulic cylinder, which allows damped axial displacements, divides into an inferior and a superior cylinder, which are slideably fixed to each other. The inferior cylinder fixedly attaches to the plane bearing and the superior cylinder attaches fixedly to the bottom surface of the multi-curvate ball-and-socket joint. The multi-curvate "ball" interlocks with the superior vertebral plate while retaining three (3) independent degrees of rotation. Thus, all the elements remain attached to one another and the vertebral plates throughout natural FSU motion. In a further embodiment, the vertebral plates can be rigidly fixed to the superior and inferior vertebrae of a Functional Spinal Unit (FSU) or, with obvious modification of the device's vertebral plates, modularly fixed to such plates, as disclosed in U.S. Pat. No. 7,361,192 (Doty), which is hereby incorporated by reference. In a still further embodiment, displacements along the axial axis, which is used herein to refer to a line perpendicular to the axial plane of the FSU (not the patient body axial axis), arise from compressing a spring-dashpot element that also constitutes a central axial prismatic joint whose components constitute a central shock absorbing system. Hydraulic portals within the device can also provide shock absorbing characteristics, while at the same time forcing a bio-lubricant, or other substance, to flow through and around the components of the device. This axial prismatic joint, which includes a combined dual cylinder and a spring stack, provide a column element that resists shear forces and promotes the rotation and translation of the various joint elements when the FSU is subjected to shear forces.

To further assist with shock-absorption, a flexible, double-layered, fiber-reinforced elastomer boot can be utilized to surround the functional elements of the prosthetic device. The boot can further be sealed such that surrounding bodily fluids cannot contact the functional elements of the prosthetic device. In still a further embodiment, the sealed boot can contain fluids or other substances to lubricate the functional elements of the prosthetic device. The central prismatic joint, can further act as a hydraulic pump, to help divert compression shocks to the walls of the boot, causing the boot to bulge or otherwise distort in shape and absorb some of the energy of the shock.

To further assist the boot and central cylindrical joint in resisting shocks and arbitrary FSU force loads, an internal toroidal-belt cushioning element can be utilized with the subject invention. Thus, the present invention provides an articulated, modular six-Degrees-of-Freedom (6-DOF) spatial mechanism for intervertebral spinal disc prosthesis that provides highly advantageous generally normal spatial motion between upper and lower vertebrae of an FSU with static and dynamic load capabilities.

The device of the subject invention can be used to assist in maintaining natural spinal flexibility and motion during simultaneous, dynamically changing, curvilinear axial, lateral and sagittal rotations and translations, regardless of the details and wide variations of that motion in a patient.

The unit can also assist in accommodating variable disc spacing under static and dynamic load during normal FSU operation. For example, the disc spacing under static load in the normal spinal position can be selected by adjusting certain components of the device. The invention can absorb compression shocks, sustain static loads, respond to dynamic loads, assist in alleviating spinal cord and nerve root compression, resist torsion and extension forces and reduce excessive facet joint stress and wear.

The mechanism's components, when coupled together, form a device that preserves its own mechanical integrity, connectedness (i.e., inseparable kinematic chain), and motion properties throughout the biologically constrained motion space (i.e., the workspace) of the FSU. The complete generality of the device allows modification of the range of motion parameters and workspace, physical size, material composition, and mechanical strength to suit ordinary mechanical applications as well as spinal disc prosthetics.

The complete 6-DOF motion capability of the prosthetic disc linkage mechanism can allow natural motions dictated by the muscles and ligaments of the spine. Throughout normal motion, the system of the subject invention stabilizes the FSU because of its ability to maintain continuity of mechanical connection between the superior and inferior vertebrae while at the same time providing load bearing and permitting motion only within the nominal disc operating range or workspace. The mechanical continuity is realized by a kinematic chain of inseparable jointed elements.

The FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{nd}$ Addition, 1997). However, these angle limits do not reveal the underlying complexity of motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474 demonstrates this complexity in the cervical spine, even when the motion is restricted to flexion and extension.

In light of the above observations and limitations, the subject invention is able to accommodate a broader range of motions than other designs in a novel way, while maintaining disc stability and integrity under static and dynamic loads.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. It should also be understood that the drawings presented herein may not be drawn to scale and that any reference to or implication of dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 5 shows an embodiment of the invention, without the boot, in full flexion, that is, maximum rotation of 12-1 about the sagittal axis through the common center of a multi-spherical "ball and socket" joint 11-1 (see FIG. 4). In this position the superior vertebral plate 12-1 has translated and rotated with respect to the inferior vertebral plate 1-1 and the superior hydraulic cylinder wall 6-1 has collapsed over the inferior hydraulic cylinder wall 5-1 in a telescoping manner.

FIG. 6 shows an embodiment of the invention, without the boot, in normal position wherein the superior 12-1 and inferior 1-1 vertebral plates parallel each other and the superior hydraulic cylinder wall 6-1 slides tip to reveal some of the inferior hydraulic cylinder wall 5-1 and the interior spring elements 10-1.

FIG. 7 shows an embodiment of the invention at full extension with the superior hydraulic cylinder wall 6-1 at its maximum extension with respect to the inferior hydraulic cylinder wall 5-1. In a preferred embodiment the two cylinders have locking center elements to accomplish this function.

FIG. 8, FIG. 9, and FIG. 10 illustrate a bootless, cutaway of the invention in flexion, normal and extension as shown in FIG. 5, FIG. 6, and FIG. 7. The cutaway is in a plane parallel to the sagittal plane but not through the center of the device. A spring element 10-1 opposes the collapse of the superior hydraulic cylinder walls 6-1-1 over the inferior hydraulic cylinder walls 5-1-1. The two hydraulic cylinder wall elements slideably move along their matching wall surfaces without interference. The term multi-curvate "ball" element 11-1 refers to the two "curvate" or spherical surfaces 11-1-1 and 11-1-3 with a common center but different radii of curvature (refer to FIG. 26). A portion of the edge of hemisphere 11-1-1 projects into cavity 12-1-8 and projection 12-1-5 into cavity 11-1-8 at maximum rotation about a fixed axis through the common center of the hemispheres. Thus, the interaction of the multiple hemispheres with surfaces on the superior vertebral plate can prevent removal of the superior vertebral plate and can serve as a means for limiting joint rotation.

FIG. 35, FIG. 36, and FIG. 37 illustrate how the subject invention can be inverted in an FSU and still function as intended. Here, 12-1 becomes the inferior vertebral plate and 1-1 becomes the superior vertebral plate. This diagram shows the inverted subject invention in full flexion (FIG. 35), normal position (FIG. 36), and full extension (FIG. 37). Said configurations correspond to those of the non-inverted subject invention in FIG. 8, FIG. 9, and FIG. 10.

DETAILED DISCLOSURE

Figure 1:
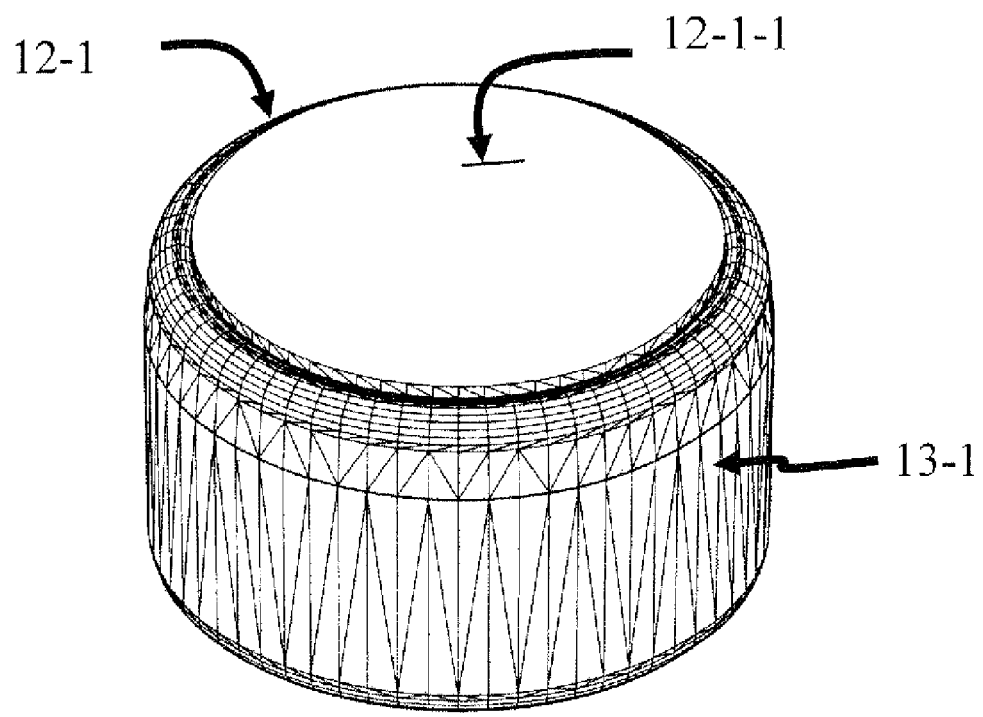
FIG. 1 depicts one embodiment of an assembled disc prosthesis of the subject invention in perspective. Visible elements of this embodiment, shown in this view, include the superior vertebral plate 12-1, the double-layered, fiber-reinforced, resilient boot 13-1. The boot hides the inferior vertebral plate 1-1 from this view.

The subject invention provides embodiments of intervertebral disk prostheses. More specifically, the subject invention pertains to one or more embodiments of an intervertebral disk prosthesis capable of providing up to 6 degrees of freedom.

The subject invention is particularly useful for the treatment of spinal disk herniation. However, a person with skill in the art will be able to recognize numerous other uses, medical or otherwise, that would be applicable to the devices and methods of the subject invention. Thus, while the subject application describes a use for treatment and/or removal of spinal disk herniation, other modifications apparent to a person with skill in the art and having benefit of the subject disclosure are contemplated to be within the scope of the present invention. As used in the subject application, "kinematic chain", "kinematic linkage", and "kinematic connection" refer to a mechanical linkage inseparably connecting the components of the device of the subject invention. It is known to those with skill in the art that a 'mechanical linkage' is a series of physical links connected with joints to form a closed chain, or a series of closed chains. Thus, as will be described herein, the components of the device of the subject invention are inseparably linked, such that the components can move relative to each other, but do not become separated one from the other. That is, when installed in an FSU, the components of the device of the subject invention remain interconnected or physically attached at all times to each other during the relative motion of the vertebrae.

The term "patient" as used herein, describes an animal, including mammals to which the systems and methods of the present invention are applied. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

Also, as used herein, and unless otherwise specifically stated, the terms "operable communication" and "operably connected" mean that the particular elements are connected in such a way that they cooperate to achieve their intended function or functions. The "connection" may be direct, or indirect, physical or remote.

The present invention is more particularly described in the following examples and embodiments that are intended to be illustrative only since numerous modifications and variations therein will be apparent to those skilled in the art. As used in the specification and in the claims, the singular for "a," "an" and "the" include plural referents unless the context clearly dictates otherwise.

With reference to the attached figures, which show certain embodiments of the subject invention, it can be seen that the subject invention (as shown, for example, in FIG. 1, FIG. 3, FIG. 4, FIG. 11, and FIG. 32) provides, in general, a multi-curvate "ball and socket" joint, prismatic central hydraulic cylinder and planar bearing. A novel implementation 1) allows six-degrees-of-freedom throughout the Functional Spinal Unit (FSU) workspace while simultaneously allowing bearing compressive, tension and torsion loads; 2) maintains the integrity of the variable intervertebral spacing required (for example, under compression the intervertebral gap should narrow some and under tension it should widen some); and retains an unbroken (fully connected at all times) mechanical linkage between the superior and inferior vertebra during any normal motion of the affected FSU, the later can promote joint stability and assist in preventing spondylolisthesis of the FSU. When appropriately scaled, the invention is capable of tracking arbitrary three-dimensional translational and three-dimensional rotational motions of the superior vertebra with respect to the inferior vertebra. In a human patient, this can include an FSU from spinal discs C2-C3 down to L5-S1, while adjusting the disc height and accommodating the various forces and moments-of-force applied to the FSU during any motion. However, the subject invention can accommodate the workspace of any FSU along the spine of a patient.

A multi-curvate "ball-and-socket" joint, a prismatic central hydraulic cylinder and a planar bearing in the base of the subject invention can permit motion from one to six degrees of freedom throughout the workspace of the FSU. The range of motion for the multi-curvate "ball-and-socket" joint, in an embodiment where the curvate surfaces are portions of spheres having a common center, can be between approximately 0 to approximately ±15 degrees of rotation about any axis through the common center of the spherical surfaces. The planar bearing can slide laterally between approximately 0 to approximately ±1.5 millimeters of displacement and sagittally between approximately 0 to approximately ±1.5 millimeters of displacement, independently. The superior part of the hydraulic cylinder can slide between approximately 0 to approximately ±1.5 millimeters axially. The numbers here are suitable for cervical FSUs, but can be scaled for larger FSUs, such as, for example, L5-S1. All rotation and slider joints in the invention can be mechanically programmed with judicious choice of joint limit stops, including cushioned stops to reduce impact wear on the stops. A person with skill in the art and having benefit of the subject disclosure would be able to devise appropriate stops that can be used with the embodiments of the subject invention. Such variations are considered to be within the scope of the subject invention.

In one embodiment, a central hydraulic cylinder spring-dashpot system offers both static and dynamic stability to the FSU with shock absorbing characteristics. The central hydraulic cylinder can slide sagittally and laterally, independently or simultaneously, with the plane bearing within the inferior vertebral plate. The relative motion of the central hydraulic spring-dashpot with respect to the inferior and superior vertebrae of an FSU and its interior spring elements allow it to generate an opposing force to any compressive static or dynamic load acting on the sliding axial axis of the FSU, regardless of the position of the vertebrae and the complex motion involved. Non-axial components of the force can act to rotate the superior vertebral plate about the multi-curvate ball and socket joint and translate the remainder of the prosthesis until any joint limit stops in the device rigidly oppose any further motion in that particular direction or orientation. A protective boot and toroidal belt assist in the hydraulic and shock absorption properties. Additional cushioning elements can also be used to enhance shock absorption.

In an embodiment of the subject invention, an element with multi-spherical surfaces constitutes the top of the hydraulic cylinder and, in conjunction with appropriate cavities in the superior vertebral plate, form a "ball-and-socket" type of curved joint which allows rotation of the superior vertebral plate with respect to the hydraulic cylinder about any axis passing through the common center of the hemispheres. Since arbitrary 3-D rotations can be reduced at each instant to a rotation about some axis, such a rotation joint can accommodate any dynamically varying 3-D rotation within the constraints of motion dictated by the device structure. The design of this special "ball-and-socket" can incorporate features that limit the amount of rotation about any axis, including the axial axis. In contrast, a typical ball and socket usually permits spinning the ball within the socket, without angle constraint, about at least one axis. In a further embodiment, of the multi-curvate "ball-and-socket" joint, the surfaces do not have to be hemispheres in order for the "ball" or curved element to be operably locked into the socket, that is, the "ball" will not pull out of the socket during operation, thus, preserving the kinematic connection to the "socket" during operation.

The inclination of the invention with respect to the body coordinates depends upon the natural inclination of the FSU to the body planes. Specifically, the invention should be inserted into an FSU, with the disc removed, such that the superior and inferior surfaces of the subject invention are parallel to the FSU vertebral surfaces of a patient in the normal posture. Such placement can maximize the effective work space of the prosthesis.

In the description to follow, the axes of motion are defined with respect to the subject invention and referred to as the sagittal, lateral, and axial axes. To keep motion descriptions simple, the text will refer to the axes of the subject invention and not to those of the FSU or the patient body.

A particular embodiment of the spinal disc prosthesis of the subject invention is operated by the muscles and ligaments of the spine when installed in an FSU. These muscles and ligaments drive the spring-damping system and resultant motion of the prosthesis. The kinematic generality of the motion capabilities of the prosthesis, allows natural movements of any or all FSUs along a spine in which appropriately dimensioned prostheses are placed.

Figure 13:
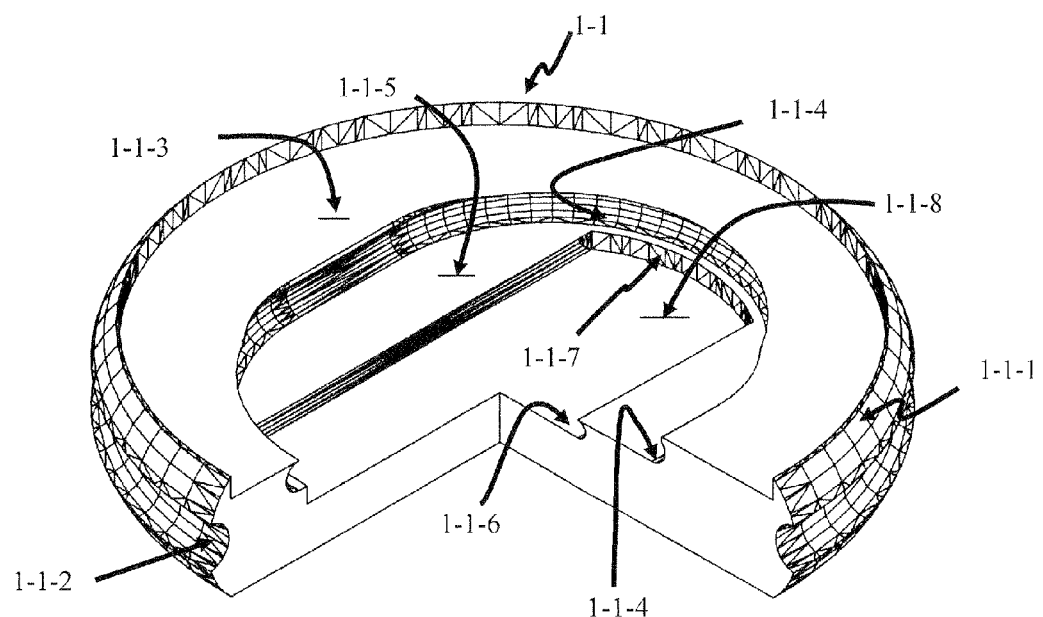
FIG. 13 shows an embodiment of the inferior vertebral plate, illustrating its different structures and surfaces by means of a tilted perspective view of the plate with a quadrant cutaway.

In one embodiment, the three joint axes (15-1, 16-1, 17-1, FIG. 11 and FIG. 13) are mutually orthogonal, providing three independent degrees of freedom for translation along the sagittal axis 15-1, lateral axis 16-1, and the central axial axis 17-1 of a central hydraulic cylinder. Another embodiment allows three degrees of rotation about a multi-curvate "ball-and-socket" joint center, which moves as the central hydraulic cylinder compresses and expands. In one embodiment, the sagittal axis 15-1 and the lateral axis 16-1 are fixed relative to the inferior vertebral plate 1-1, hence, by rigid unbroken connection, to the inferior vertebra of the FSU. The axial axis 17-1 is normal to the plane of the sagittal and lateral axes and moves, for arbitrary motions of the superior vertebra of the FSU, with respect to its inferior vertebra.

The Instantaneous Axis of Rotation (IAR) of an FSU often changes during the motion of the superior vertebra with respect to the inferior vertebra. The IAR of an embodiment of a multi-curvate "ball and socket" joint moves with the compression and expansion of the central hydraulic cylinder, as well as with the plane motion of the planar bearing, but it is always on the axial axis 17-1. The locus of the IAR, in one embodiment, lies within a rectangular volume traced out by the slider joints of approximately 3 mm by approximately 3 mm by approximately 2.5 mm (Width×Length×Height). Scaled versions can accommodate smaller or larger ranges of motion, as any person skilled in the art can realize. Since this volume falls within the inferior vertebral plate body, the IAR locus is confined at all times within the volume of the subject invention. In one embodiment, rotations of the multi-curvate "ball-and-socket" joints alone are not kinematically sufficient to mimic natural motion of an FSU. However, the translation capabilities of the slider axes, the planar joint and the central hydraulic cylinder slider joint, can compensate for the differences in displacements induced by IARs outside of the subject invention's volume. In this manner, this embodiment of the subject invention provides the same FSU motion capabilities generated by a moving IAR whose locus of motion is inside and/or outside of the normal vertebral spacing without needing to duplicate the means by which the spine generates such FSU motion.

Figure 12:
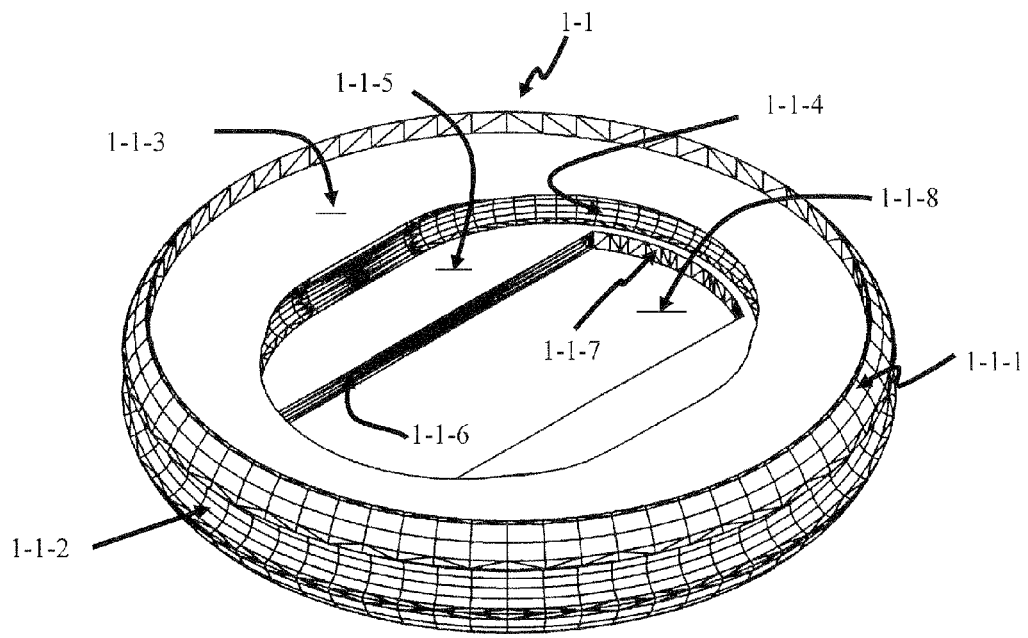
FIG. 12 illustrates an embodiment of the inferior vertebral plate, including its different structures and surfaces by means of a tilted perspective view of the plate. In this embodiment, the concave curvate surface 1-1-4 conforms to the convex curvate surface edges of the planar bearing platform 2-1. Further, the planar bearing cap lock 4-1 fixedly attaches to surface 1-1-3 to slideably lock the planar bearing platform to the inferior vertebral plate 1-1. The inside vertical surface of feature 1-1-1 can be keyed with outer curvate edge of 4-1 to align the cap lock. The keying is not shown in the diagram, but can easily be implemented by any one skilled in the art, for example, by one or more slots on the inside vertical surface of 1-1-1 matched by conforming tabs on the curvate edge of 4-1.
Figures 14A, 14B:
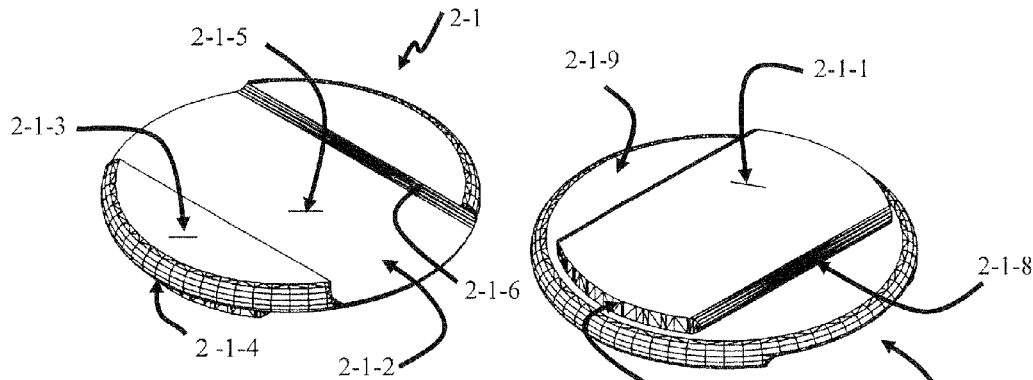
FIGS. 14A and 14B show perspective views of the top (FIG. 14A) and bottom (FIG. 14B) of an embodiment of the sagittal-lateral planar bearing platform. In this embodiment, convex curvate edge 2-1-4 conforms to concave curvate edge 1-1-4 when the platform 2-1 comes into contact with 1-1. Further, convex curvate edge 2-1-7 conforms to concave curvate edge 1-1-7 when 2-1 comes into contact with 1-1. Surface 2-1-1 can conform to surface 1-1-8 within the sagittal prismatic raceway cavity, the complex cavity in 1-1 that accommodates the motion of the sagittal bearing surfaces, and slide along surface 1-1-8. Convex curvate surface 2-1-8 can conform to concave curvate surface 1-1-6 also within the sagittal prismatic raceway cavity, slideably locking the planar bearing platform to the inferior vertebral plate 1-1.
Figure 16:
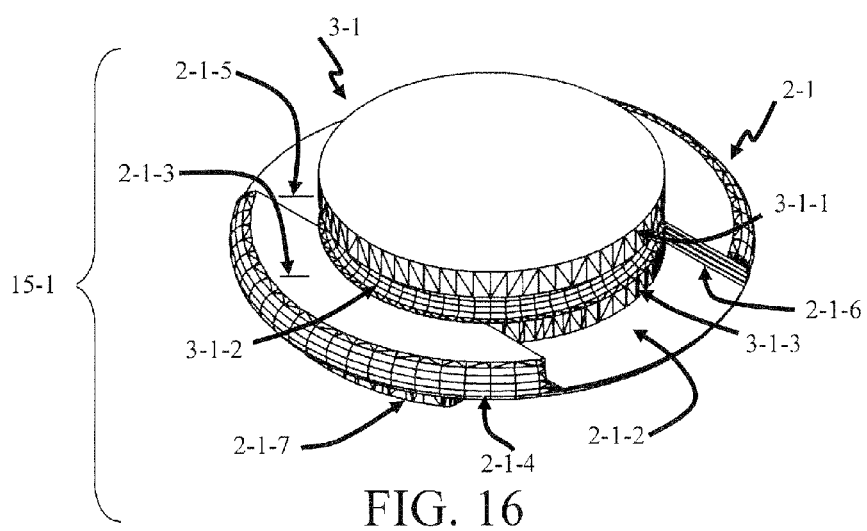
FIG. 16 depicts an embodiment of the sagittal-lateral plane bearing assembly 15-1 wherein the lateral bearing element 3-1 is slipped into raceway 2-1-2 of element 2-1.
Figure 17:
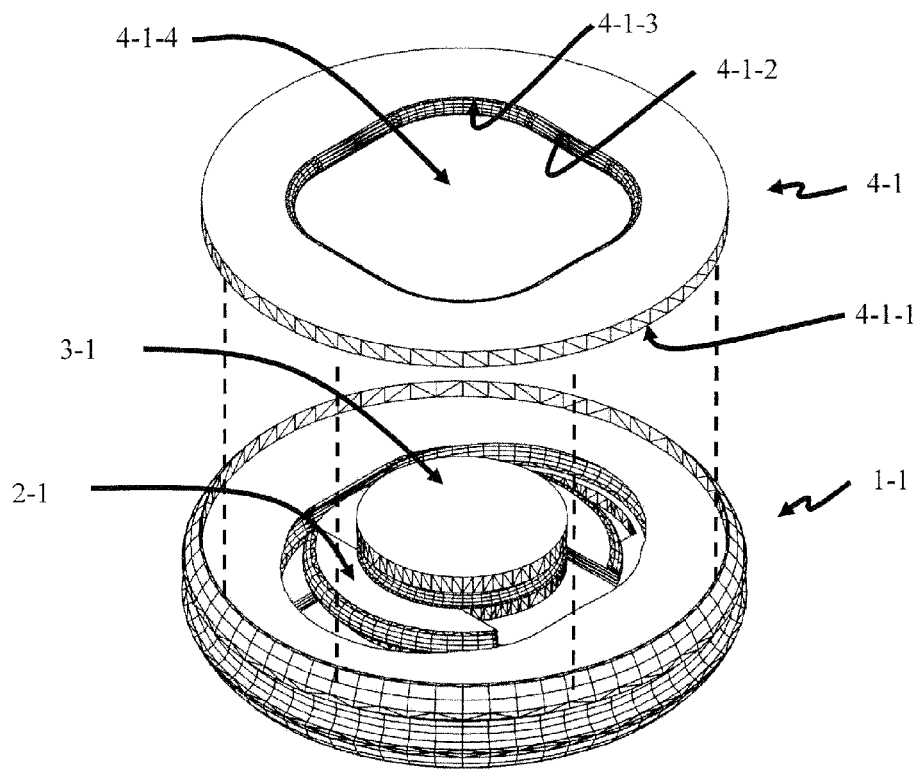
FIG. 17 is a perspective, partially exploded view of an embodiment of the planar bearing assembly 15-1 operably positioned within the cavity of the inferior vertebral plate 1-1, illustrating how the planar bearing guard ring 4-1 fits fixedly into 1-1. In this embodiment, the dimensions of the opening 4-1-4 of 4-1 is such that the assembled elements 2-1 and 3-1 of the planar bearing cannot be disengaged from the inferior vertebral plate 1-1.
Figure 18:
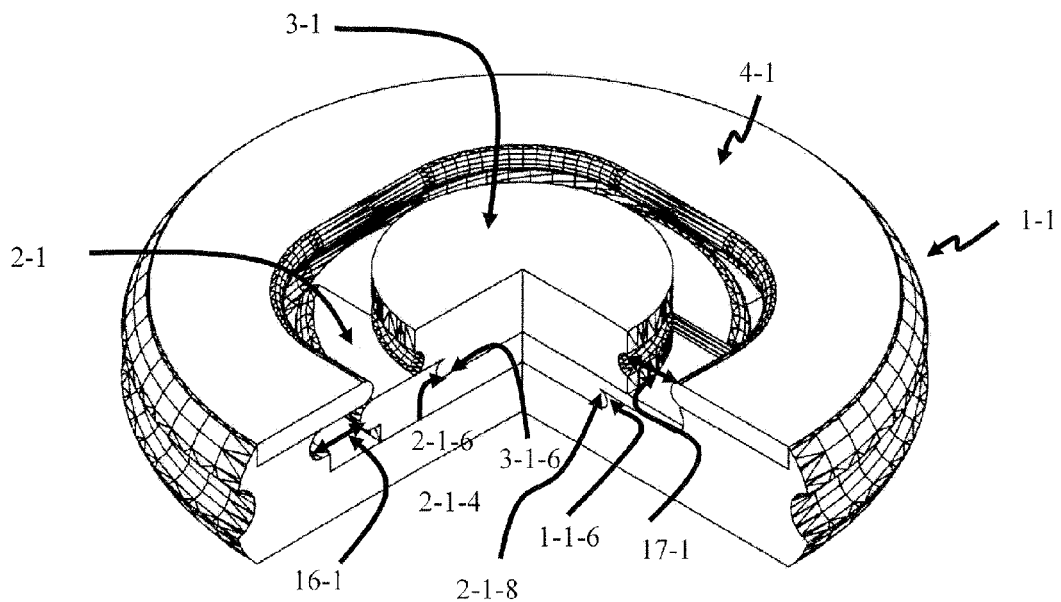
FIG. 18 shows a quadrant cutaway view of an embodiment of the planar bearing assembly 15-1 operably attached within the inferior vertebral plate 1-1. The sagittal motion of the planar bearing realized by elements 2-1 and 3-1 in this embodiment is indicated by sagittal axis 16-1. Lateral motion of this planar bearing is indicated by lateral axis 17-1.

In a specific embodiment of the subject invention, a lateral and sagittal movement are attained with a planar joint configuration (FIG. 17 and FIG. 18), that includes an inferior vertebral plate 1-1 (FIG. 12 and FIG. 13) and a planar bearing assembly (FIG. 16) operably attached therein. The planar bearing assembly (FIG. 16) includes a lateral-sagittal planar bearing element 2-1 (FIGS. 14A and 14B), a lateral bearing element 3-1 (FIGS. 15A and 15B) and a planar bearing guard ring 4-1. The lateral-sagittal planar bearing element slides along the sagittal direction 16-1 and carrying the lateral bearing element 3-1, and anything attached to 3-1, in that direction until convex surface 3-1-2 (FIG. 16) encounters conforming concave surfaces 4-1-3 or 4-1-2 of the planar guard ring 4-1 (FIG. 17). The dimensions of the opening 4-1-4 and the planar bearing element 2-1 can prevent the planar bearing element 2-1 from pulling out of the planar socket. In a particular embodiment, the planar surface 1-1-3 and the cylindrical inside wall of curvate surface 1-1-1 (FIGS. 12 and 13) conform to the underneath planar surface of 4-1 and the cylindrical edge surface 4-1-1 to allow fixedly attaching 4-1 to 1-1 (FIG. 17).

In one embodiment, the surfaces of the sagittal-lateral planar bearing platform conform to one or more surfaces of the lateral bearing platform. In a specific embodiment, the surface 1-1-7 conforms to the end surfaces 2-1-7 at the maximum reach of the sagittal slide on either end. The planar surface 2-1-1 can conform to planar surface 1-1-8 within the sagittal prismatic raceway cavity of inferior vertebral plate 1-1. The surfaces 1-1-5 and 2-1-9 can conform and can make the sagittal bearing surface larger when designed to contact each other. The convex surface 2-1-4 can conform to concave surfaces 1-1-4. Within the sagittal prismatic raceway cavity of inferior vertebral plate 1-1, the concave surface 1-1-6 and conforming convex surface 2-1-8 can also lock 2-1 to 1-1.

In a further specific embodiment, opening or groove 2-1-2 provides the lateral raceway for the lateral bearing element 3-1 (FIG. 15A, FIG. 15B and FIG. 16), in which planar surfaces 2-1-5 and 3-1-5 conform. Surfaces 2-1-3 and 3-1-7 can conform and can extend the lateral bearing surface when designed to be in contact. In a still further specific embodiment, the concave surfaces 2-1-6 conform to convex surfaces 3-1-6 to lock element 3-1 into 2-1. Curvate surface 3-1-3 can be configured so as to not interfere with surface 1-1-4 at either end of the maximum lateral move along axis 17-1.

Figure 19:
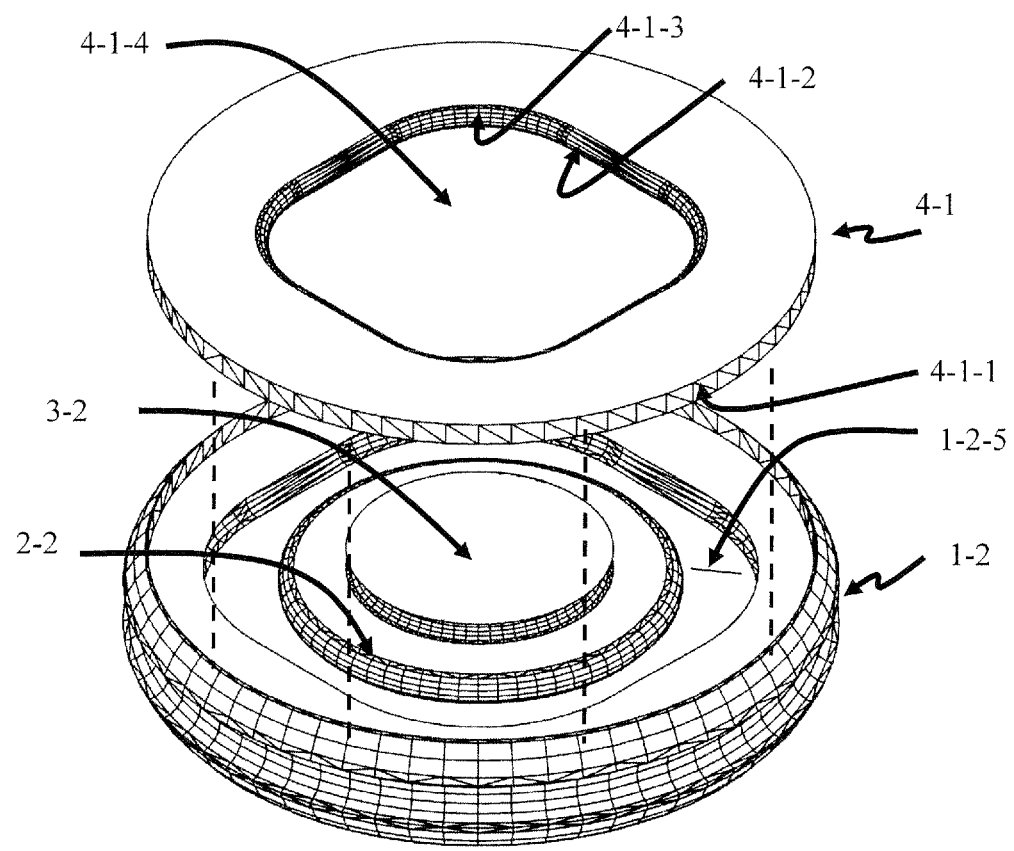
FIG. 19 depicts another embodiment of the planar bearing. In this embodiment, the element 4-1 does not change from the previous embodiment. Elements 1-2, 2-2 and 3-2 do differ from their counterparts 1-1, 2-1 and 3-1, however. Elements 2-2 and 3-2 move as a unit on the planar surface 1-2-5 of 1-2 and are fixedly attached to each other or manufactured as a single piece. The edge surfaces conform as in the previous embodiment. In this embodiment the planar bearing can rotate freely about the central axis of 2-1 and 3-1, namely, the perpendicular to the plane of 1-2-5 passing through the center of 3-1. The planar bearing guard ring 4-1 serves the same purpose as in the previous embodiment, namely, to prevent the separation of the plane bearing joint.

In an alternative embodiment of the planar joint (FIG. 19), elements 3-2 and 2-2 are fixed together, or formed into a single element. The bottom surface of 2-2 is substantially planar and slides on a planar "socket" surface 1-2-5 of this embodiment of the inferior vertebral plate 1-2. As before, all edge surfaces can conform at the extremes of sagittal and lateral translations. This embodiment allows translations of the center of the bottom disc 2-2 to any point in the plane of the bearing, with the sagittal displacement between approximately 0 and approximately ±1.5 mm and the lateral displacement between approximately 0 and approximately ±1.5 mm as referenced to the centroid of the planar socket of 1-2. The planar guard ring 4-1 structure and its function can remain the same in this embodiment.

Figure 27:
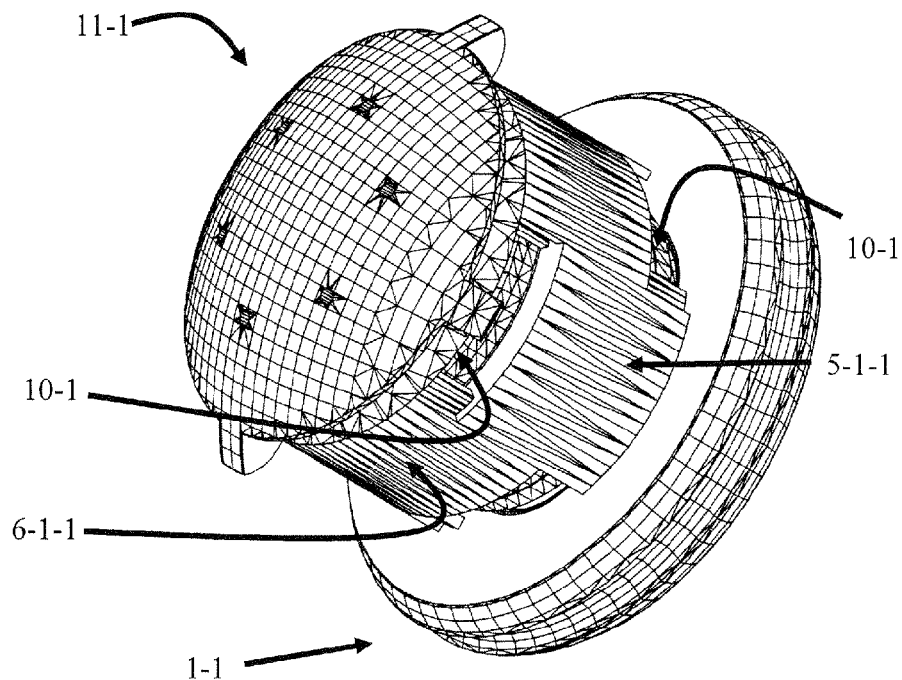
FIG. 27 is a side perspective view of an embodiment of the subject invention in normal position, without the boot, toroidal belt, and the superior vertebral plate. The gaps in the central cylinder, generated by sliding the walls edge-to-edge, can act as hydraulic portals. At full compression, all the wall gaps disappear and only portals 11-1-4 and 9-1-2 allow the passage of fluid into or out of the central hydraulic cylinder.
Figure 28:
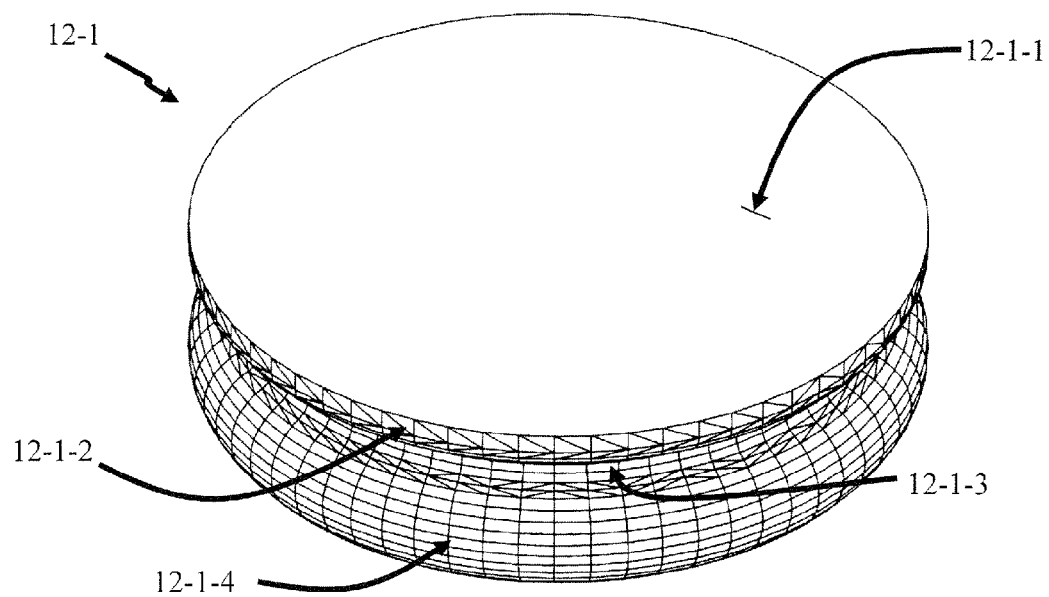
FIG. 28 is a perspective view of an embodiment of the superior vertebral plate 12-1.
Figure 29:
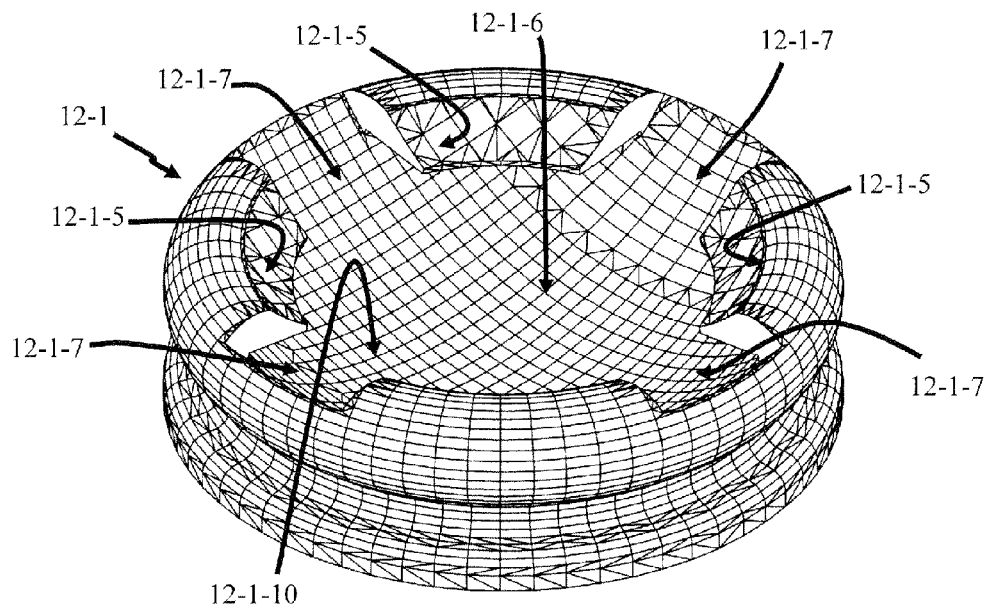
FIG. 29 and FIG. 30 illustrate the various curvate surface of the underside of an embodiment of the superior vertebral plate 12-1 that conform to the complex curvate surfaces of 11-1.
Figure 30:
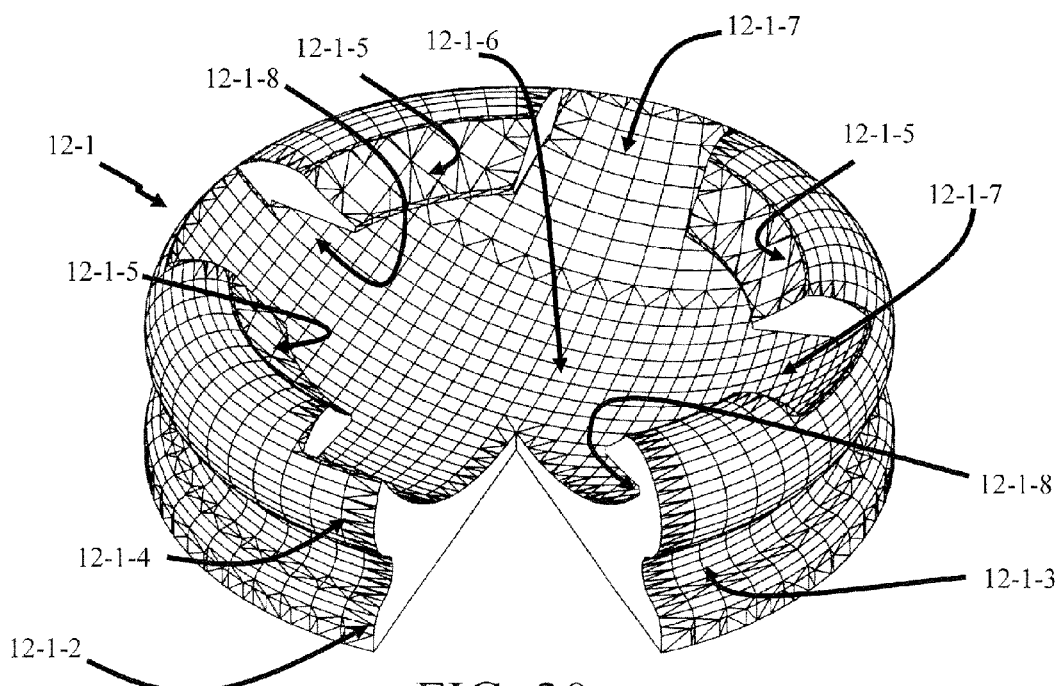

A further embodiment incorporates a central hydraulic cylinder (FIG. 11, FIG. 20 and FIG. 21), with inner and outer sliding wall segments, that includes an inferior and superior hydraulic cylinder. In this embodiment, the inferior hydraulic cylinder is composed of elements 5-1, 7-1, 3-1 and 9-1. Curvate edge 3-1-1 can conform to the inside edge of base ring 9-1 so that platform 3-1 press fits into cavity 9-1-1 of element 9-1, or can be otherwise fixedly attached to 9-1, by any of a variety of methods known to those with skill in the art. Thus, the lateral bearing upper surface 3-1-4 and the top surface of base ring 9-1 can be the platform base for spring elements within the inferior hydraulic cylinder, discussed in detail below. A superior hydraulic cylinder can be composed of elements 6-1 and 8-1. In a further embodiment, a multi-curvate "ball" 11-1 (FIG. 25) can be fixedly attached to the top of 6-1 and 8-1. The subject invention without plate 12-1 (FIG. 27) illustrates how 11-1 caps the central hydraulic cylinder.

Element 5-1, mentioned above, can be configured with two, three, or more wall segments 5-1-1 which slide with respect to the two, three, or more wall segments 6-1-1 of element 6-1. The sliding joint between the walls in a particular embodiment can be a sliding mortise-and-tenon joint. In an alternative embodiment, a sliding lap joint (FIG. 24) can be utilized to slidably join the walls. Alternative embodiments can utilize any variety of sliding joint types between wall segments known to those skilled in the art. Such alternative embodiments are contemplated to be within the scope of the subject invention.

Element 7-1 can also be configured with two, three or more wall segments 7-1-1 which slide with respect to two, three or more wall segments 8-1-1 of element 8-1. The slider joints between the wall segments 7-1-1 and 8-1-1 can, but do not have to, be the same as those of the outer walls. In one embodiment, for inner wall segments, mortises 8-1-2 slide along tenons 7-1-3 running the length of wall segments 7-1-1, but the outer wall segments joints can be lap joints. Of course, the inner cylinder core wall segments could also form lap joints. These illustrations in no way limit the variety or combinations of inner and outer wall joints types easily envisioned by one skilled in the art. Any and all such variations known to those with skill in the art are considered to be within the scope of the subject invention.

Figures 15A, 15B:
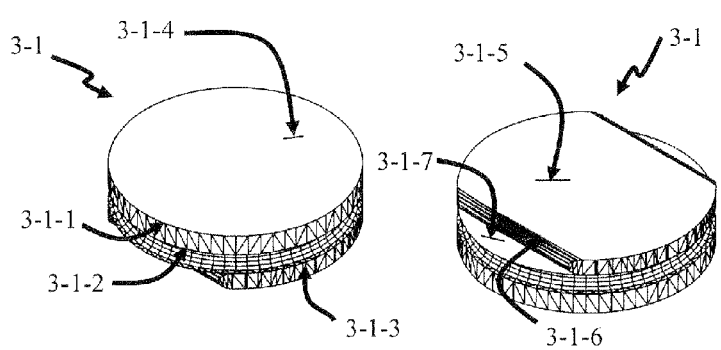
FIGS. 15A and 15B show perspective views, from left (15A) to right (15B), of the top and bottom of an embodiment of the lateral bearing platform 3-1. In this embodiment, curvate edge 3-1-1 conforms to the inside edge of 9-1. Lateral bearing Platform 3-1 is positioned within, such as by press fitting, central opening 9-1-1 of element 9-1, or is otherwise fixedly attached to 9-1. Further, concave curvate surface 3-1-2 can conform to convex curvate inner surfaces 4-1-2 and 4-1-3 of planar bearing guard ring 4-1. Bearing surface can slide along raceway 2-1-2 of the sagittal-lateral plane bearing platform 2-1. Concave curvate bearing surfaces 3-1-6 can conform to convex curvate bearing surfaces 2-1-6 allowing lateral bearing element 3-1 to slideably lock into 2-1.
Figure 22:
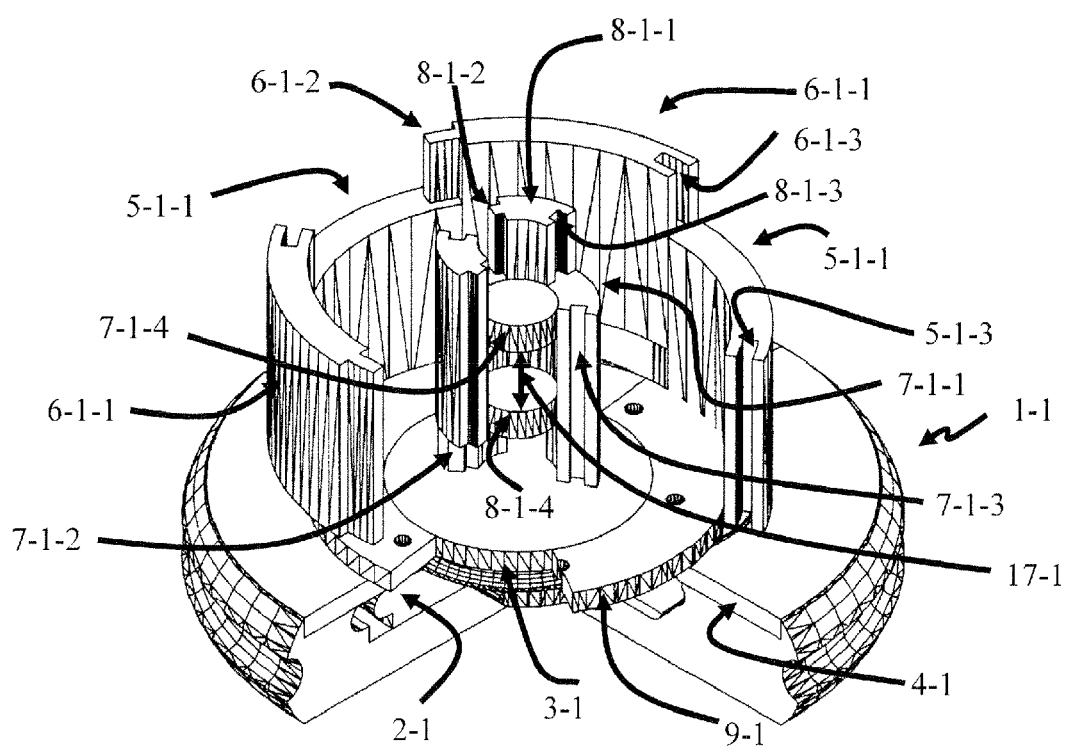
FIG. 22 is a quadrant cutaway perspective view of an embodiment of the lower assembly of the device resulting from fixing the central hydraulic cylinder onto element 3-1. Spring elements within the cylinder, one wall segment 5-1-1, and one wall segment 6-1-1 have been removed to reveal the subassembly more fully.
Figure 23:
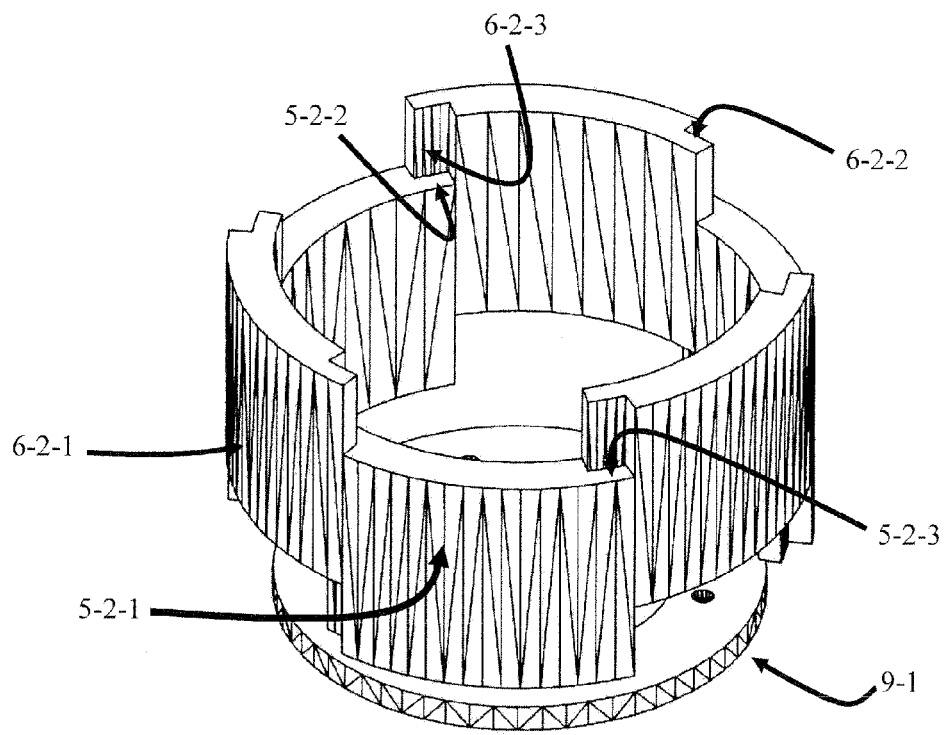
FIG. 23 shows another particular embodiment of the slidably joined segmented central cylinder outer walls. In this embodiment, the sliding joint is a lap joint instead of mortis-and-tenon: 5-2-3 laps with 6-2-2 and 6-2-3 laps with 5-2-2.
Figure 25:
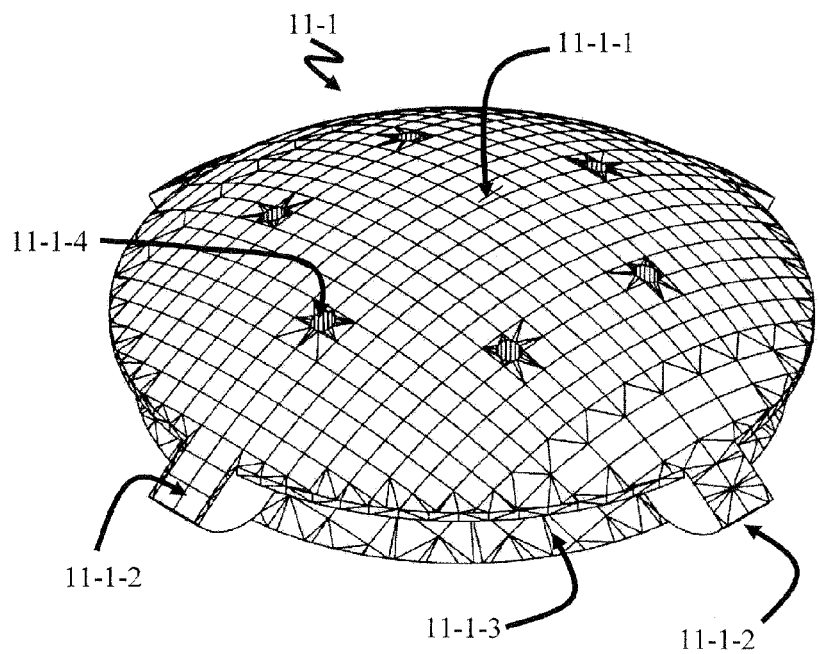
FIG. 25 illustrates the top perspective view of an embodiment of a multi-curvate surfaced "ball joint" 11-1 with integrated rotational joint stops 11-1-2 and hydraulic portals 11-1-4. In this embodiment, spherical surfaces 11-1-3 and 11-1-1 have the same center but different radius of curvature.

In a particular embodiment, the bottoms of the segmented walls 7-1-1 fixedly attach to lateral bearing upper surface 3-1-4 (FIG. 22) or can be manufactured as part of element 3-1 (FIGS. 15A and 15B). The tops of wall segments 8-1-1 fixedly attach to undersurface 11-1-6 or can be manufactured as part of element 11-1 (FIG. 25).

In a further embodiment, the center post element 7-1-4 rigidly attaches at or near the top of all the walled segments of 7-1. In a still further embodiment, the center post element 8-1-4 rigidly attaches at or near the bottom of all the walled segments of 8-1 and is substantially physically below or more caudal than 7-1-4. The center posts add considerable strength to the interior wall segments which can serve as an interior support mandrel for spring elements. As the superior hydraulic cylinder slides more cranially during extension, the post element 7-1-4 can eventually interfere with further motion of 8-1-4 and the extension stops. The contact surfaces of the center posts can be cushioned. The center posts can, thus, serve as joint stops as well as structure enhancing elements. The size of the gap between the center posts at maximum compression can also define the limit of axial translation. In one embodiment, this distance can be approximately 2.5 mm.

The spinal disc prosthetic of the subject invention can constrain the relative motion of the superior vertebra with respect to the inferior vertebra to its natural locus of motion and can maintain, through the load bearing spring and cushion elements, the correct variation in intervertebral spacing during motion (see FIG. 5 through FIG. 10).

Advantageously, further embodiments of the subject application can provide 1) effective static load bearing through one or more spring elements, 2) hydraulic damping and shock absorption by means of hydraulic pumping action, 3) cushioning in the various joint axes conjoined with a general-purpose cushion element, constrained within the device by a central cylindrical core, 4) automatic hydraulic lubrication of all joints, 5) intervertebral stability and inseparability through mechanical linkage between a superior and an inferior vertebral plate that prevents motion outside the normal, natural range, 6) mechanically programmable vertebral spacing under nominal compression load-bearing by appropriate selection of spring constants, height and number in the central spring element or stack, 7) 6-DOF motion tracking with variable disc height throughout the prosthesis workspace, and 8) a mechanically programmable prosthesis workspace through judicious sizing of linear and rotational joint stops. The millimeters of linear translation allowed by the slider joint stops can be independently specified while rotation maximums about the sagittal, lateral and axial axes can be mechanically programmed for the multi-curvate ball joint, enabling the invention to match the device workspace to that of the client's FSU workspace.

The motion elements of the prosthetic device of the subject invention can be fabricated of, for example, but not limited to, titanium steel, titanium-carbide-coated stainless steel, bio-inert hardened stainless steel, polyurethane, polyurethane thermoplastic, cobalt-chromium-molybdenum alloy, plastic, ceramics, glass, or other materials or combinations thereof. In a further embodiment, the motion elements of the prosthetic device of the subject invention can be fabricated with hardened stainless steel ball-bearings and bearing rods that can move on hardened stainless steel curvate or linear rods that fit into raceway cavities of the various titanium or plastic elements. In an alternative embodiment, a combination of polyurethane thermoplastic bearings and polyurethane, titanium, ceramics, cobalt-chromium-molybdenum alloy and titanium-carbide-coated hardened stainless steel components can be utilized. A person with skill in the art having benefit of the subject disclosure would be able to determine any of a variety of materials that could be utilized for the manufacture of one or more elements of the device of the subject invention. It is contemplated that such variations are within the scope of the subject invention.

The device of the subject invention can also allow for joint limits and stops on all degrees of freedom, which permits mechanical programming of its workspace to match the FSU workspace. The invention can, thus, accommodate the wide variability of FSU motion at different locations within the spine and between spines of different patients.

In one embodiment, the modular 6-DOF spatial mechanism for spinal disc prosthesis of the subject invention comprises a superior vertebral plate 12-1 and an inferior vertebral plate 1-1. However, the subject invention insertion or installation within a spine can be inverted (as seen, for example, in FIG. 35, FIG. 36, and FIG. 37), so that 12-1 becomes the inferior vertebral plate and 1-1 the superior vertebral plate. The inverted device, in principle, functions much the same as the non-inverted version. For example, compare the subject invention in FIG. 8, FIG. 9, and FIG. 10 to FIG. 35, FIG. 36 and FIG. 37, respectively. FIG. 8 shows the subject invention in full flexion while FIG. 35 shows the inverted subject invention in full flexion. FIG. 9 shows the subject invention in normal position while FIG. 36 shows the inverted subject invention in normal position. FIG. 10 shows the subject invention in full extension while FIG. 37 shows the inverted subject invention in full extension. Practical considerations can dictate the preferred orientation within the spine.

In a further embodiment, the spinal disc prosthesis of the subject invention comprises a flexible, double-layered, boot-protected, modular and replaceable 6-DOF prosthetic disc mechanism (mechanical linkage). In one embodiment, the vertebral plates can be formed from a biocompatible material such as, for example, titanium, cobalt-chromium-molybdenum alloy, or titanium-carbide-coated stainless steel with a bone fusion matrix on the side of the plate shaped as a spherical surface to enhance surface area contact between vertebra and the vertebral plate.

Any number of techniques known to those with skill in the art may be used to embed the superior vertebral plate of the subject invention into the bone of the superior vertebra and the inferior vertebral plate into the bone of the inferior vertebra of an FSU. It is contemplated that such techniques are within the scope of the subject invention.

In a further embodiment, a flexible, double-layered boot 13-1, as shown, for example, in FIG. 1, FIG. 2A, FIG. 4, and FIG. 32) surrounds the prosthetic device of the subject invention. The boot can provide a biocompatible impermeable barrier between fluids that may be sealed within the prosthetic device, for example, a biocompatible silicone fluid or saline solution, or other suitable fluid, and fluids within surrounding tissues. In one embodiment, the boot is a sturdy, flexible and elastic material, such as, for example, corrugated materials, woven fiber materials, and elastic materials, or other non-homogeneous materials or combinations thereof. In a further preferred embodiment, the boot comprises woven, flexible fibers embedded in a strong, flexible silicon elastomer matrix that can block fluid transfer. The embedded fiber weave, in the embodiment mentioned above, can assist in torsion loading on the prosthesis as well as loading during flexion and extension. In a further embodiment, the weave direction of the embedded fibers is diagonal relative to the central axis of a spherical or right-circular cylinder embodiment of the boot structure. In a further embodiment, the boot can form a walled "tubular" structure ("double-layered"). By way of a non-limiting example, the double-layered boot can be formed by weaving fibers in a closed curve about the two clamping rings. In a still further embodiment, the boot can be quilted, with quilt pads filled with cushioning materials or different types of fluids. In a particular embodiment, a corrugated boot, is manufactured a rugged fiber elastomer designed for flexibility and toughness, assists in torsion loading on all axes and opposes extension under nominal conditions, thus, reducing nominal spinal muscle stress in the neutral position. In a further embodiment, a variety of joint limit stops can be utilized on the multi-curvate ball-and-socket rotational joint of the invention, which can act to limit the amount of torsion the boot experiences, reducing the possibility of tears from overstress.

All displacements and rotations of the joints of the subject invention can be mechanically programmed to specific joint limits by appropriately installed joint stops. The joint stops can be rigid, or, to reduce wear, cushioned with materials falling within a wide range of durometer choices from 50 to 100.

In one embodiment, the boot has asymmetric thickness, using more reinforcing fiber in the posteriorly-installed portion and less in the anteriorly-installed portion, making the anterior portion more flexible and the posterior portion less flexible, but stronger and more durable. The non-uniformity of the boot thickness allows for non-linear compression and extension. This configuration can reduce interaction with the spinal column or nerve ganglia when the boot is expanding and/or contracting. For example, as the FSU flexes, the boot can contract, primarily the highly flexible thinner sections. In a neutral position of the FSU, the boot can be under slight tension. At maximum compression of the FSU, the boot can bulge from hydraulic pressure and expanding cushioning material inside the device; however, without those pressures the boot would be slack. At maximum extension, the boot stretches, from its neutral position. In one embodiment, at maximum extension, the boot stretches an additional 20% in its anterior portion and about 10% or less in the posterior.

A further embodiment utilizes a fibrous belt or toroidal tube 19-1 (FIG. 32) as an additional cushioning element in the subject invention to assist the boot and central cylindrical joint in resisting shocks and arbitrary FSU force loads by compressing sections of the toroid. In one embodiment, the toroidal tube 19-1 is filled with compressible fluids, gels, such as, for example, hydrophilic gels or hydrogels, or other suitable materials. In an alternative embodiment, the toroidal tube 19-1 is a solid material. This tube can wrap around the central hydraulic cylinder elements and can be confined to the disc volume by same. In a further embodiment, a toroidal belt or tube can float, not be fixed to any other elements. In an alternative embodiment, a toroidal belt can attached to one or both of the vertebral plates. In a still further alternative embodiment, a toroidal belt can be integrated into the boot. With the latter embodiment, the boot and toroidal belt resembles the concept of fiber ring and cushion element as instructed by Casutt (U.S. Pat. No. 6,645,248). In one embodiment of the subject invention, the toroidal belt moves about with the central hydraulic cylinder as the cylinder translates axially, laterally or sagittally with respect to the vertebral plates. The toroidal belt can oppose the cylinder motion in all cases since it either pushes against the boot when not fixed to any elements or, if fixed to the vertebral plates, the belt pulls against those plates. Effectively, in either case, the toroidal belt can provide a three-dimensional, universal resilient or spring-like action opposing the cylinder motion. The belt can also strengthen the central hydraulic cylinder walls to provide additional sheer stress tolerance for the device.

In a further embodiment, a lubricating fluid is contained within the prosthetic device of the subject invention by the impermeable boot seal. The lubricating fluid can be pumped through fluid hydraulic portals 9-1-2, or otherwise moved around the elements of the device, by the piston action of the superior and inferior hydraulic cylinders during spinal motion. These cylinders can further contain spring element 10-1 and cushioning elements (not shown) to provide a spring-dashpot action during FSU motion.

Figure 20:
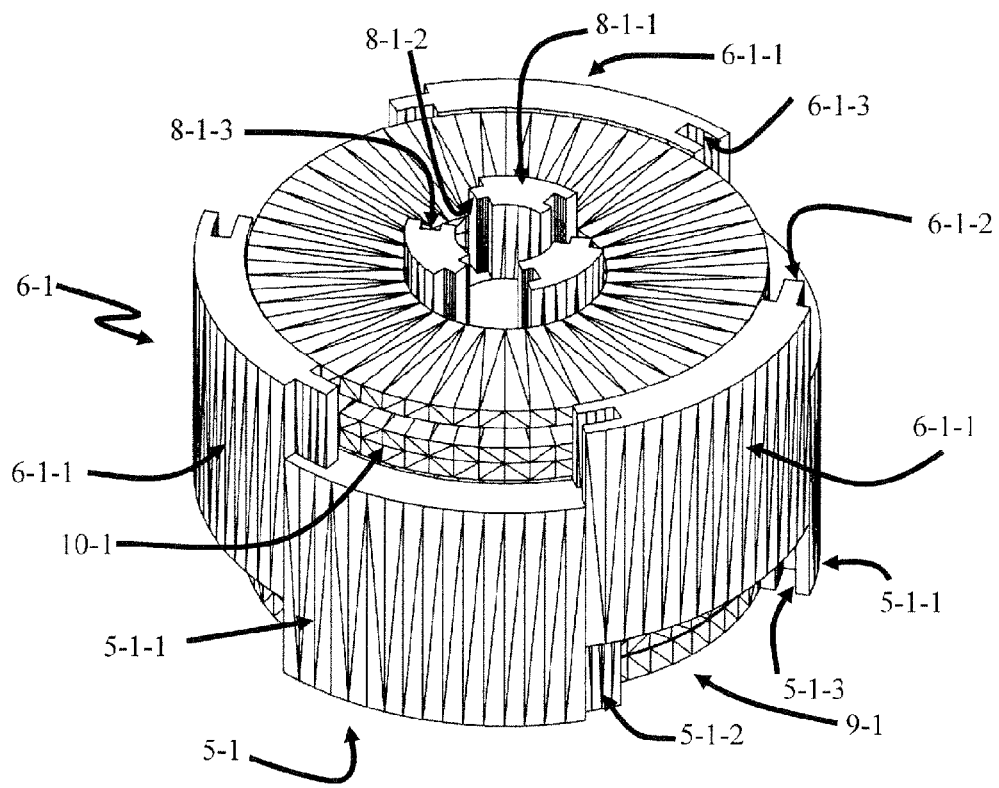
FIG. 20 illustrates an embodiment of the central hydraulic cylinder that utilizes an inferior segmented cylinder 5-1 and a superior segmented cylinder 6-1 with slideably coupled segmented walls 5-1-1 and 6-1-1 and an inner cylinder core with segmented walls. The inferior inner cylinder core cannot be seen in this figure, but the segmented walls 8-1-1 of the superior inner cylinder core 8-1 can be seen. In this embodiment, a sliding mortise-and-tenon type joint connects the walls of the various cylinders. For example, elements 6-1-2 and 5-1-3 join elements 6-1-1 and 5-1-1 into a sliding joint. The cylinder walls confine spring elements 10-1.
Figure 21:
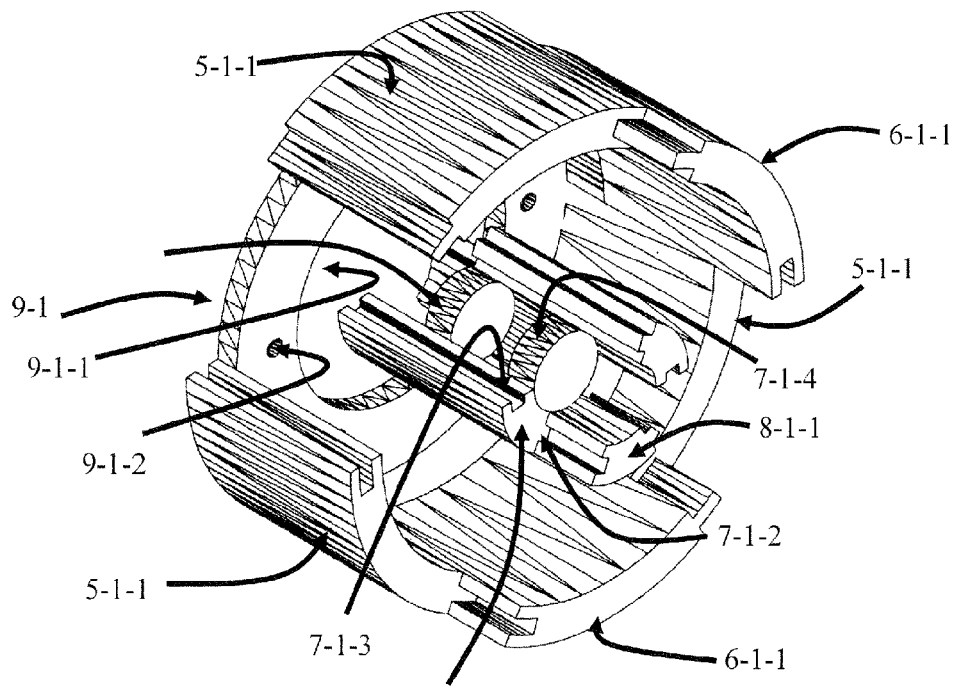
FIG. 21 shows the central hydraulic cylinder in perspective with the top cover, one wall segment 6-1-1, and the spring elements 10-1 removed. In this embodiment, the base ring 9-1 rigidly attaches or welds to the segmented walls 5-1-1. Platform 3-1 can be press-fit into opening 9-1-1, or otherwise fixedly attaches to 9-1. Convex curvate surface 3-1-1 conforms to concave curvate surface of cavity 9-1-1. Hydraulic portals 9-1-2 can serve as passages for fluids.

In one embodiment, the spring-dashpot element of the central cylindrical joint is formed by superior external walls 6-1-1 and inferior external walls 5-1-1 that slide over one another in a telescoping manner (FIG. 20). The external walls enclose a cavity that can be cylindrical in shape. The superior and inferior external walls 7-1-1 and 8-1-1 can have corresponding segmented-wall inner cores 7-1-4 and 8-1-4 (FIG. 21 and FIG. 22) that slide closer together or further apart as the external walls slide to and fro. To facilitate movement of the FSU, the inner segmented walls can mesh without interference with one another. Each gap in the superior inner core wall is matched by a solid wall segment in the inferior wall, and vice versa. The number of wall segments can vary from two, three, or more depending upon a variety of factors including, for example, the materials utilized, dimensions of the device or components thereof. A person with skill in the art would be able to determine the appropriate number of wall segments for each of the elements of the hydraulic cylinder (inner and outer lower walled segments and inner and outer upper walled segments). In a specific embodiment, the device employs three or more wall segments that are cut, molded, or otherwise formed from a solid cylindrical shape with a partial cavity, thus, forming supporting inner center posts 7-1-4 and 8-1-4 (FIG. 22) affixed to the segmented walls. The center post 8-1-4 fixedly attaches or is part of the superior inner core segmented walls 8-1-1 and all or at least a substantial portion is located below the center post 7-1-4, which is fixedly attached to the inferior inner core segmented walls 7-1-1. As the superior and inferior hydraulic cylinder walls slide past one another in extension, center post 8-1-4 will advance towards 7-1-4. Eventually, center post 7-1-4 will stop the motion of center post 8-1-4 and prevent any further separation of the inferior and superior hydraulic cylinders. The center posts of the inner core elements that come into contact can be, at least partially, configured with one or more cushioning elements mounted on rigid elements to further promote shock absorption.

In a further embodiment, the external walls and the segmented-wall internal cores can, together, firmly hold one or more spring elements in place, for example, a stack of one or more Belleville springs, in a variety of series/parallel spring configurations within the available cavity space of the central hydraulic cylinder. The number, arrangement and spring rates of the Belleville springs in the stack can determine the intervertebral spacing when the invention is under load in the spine. This allows the invention to accommodate a wide variety of patient situations by changing the composition of the spring stack. In this way, the invention can compensate for patient requirements without changing the design and/or structure of the invention elements. In effect, the spring stack composition can dictate changes for a wide range of models.

The walls of the superior and inferior cylindrical elements, along with the spring, can constitute a spring-dashpot shock absorbing system. Hydraulic portals 9-1-2 within the device can facilitate shock absorbing characteristic while at the same time force a bio-lubricant to flow through and around the components of the bearing interfaces of the device. The combined dual cylinder and the spring stack provide a column element that is able to resist shear forces and promotes the rotation and translation of the various joint elements when the FSU is subjected to shear forces.

Figure 24:
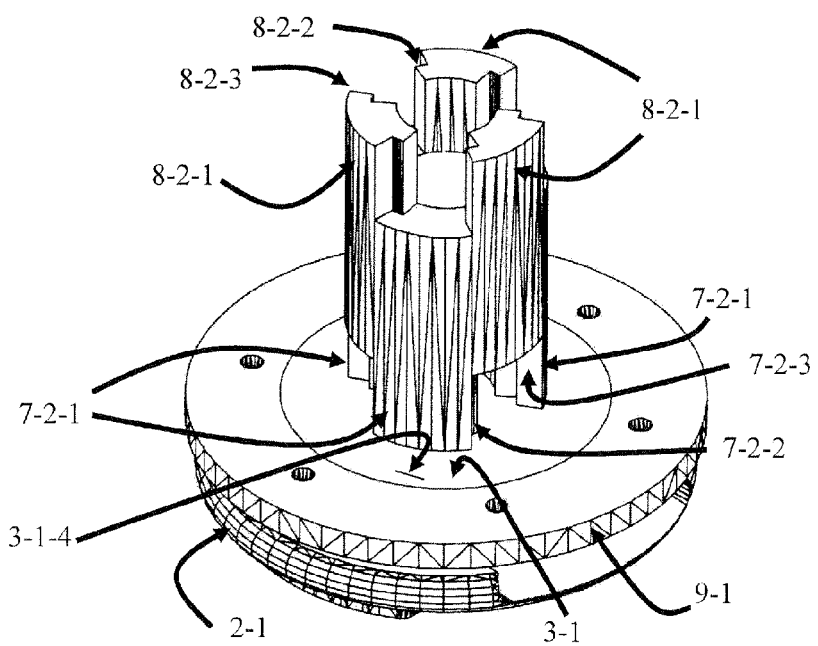
FIG. 24 shows another particular embodiment of the slidably joined segmented central cylinder inner core walls. In this embodiment, the sliding joint is a lap joint: 7-2-3 laps with 8-2-2 and 7-2-2 laps with 8-2-3. This figure also shows platform 3-1 inserted into base ring 9-1 and inner core wall segments 7-2-1 fixedly attached to lateral bearing upper surface 3-1-4.

In one embodiment, the inferior hydraulic cylinder telescopes in and out of the superior hydraulic cylinder during flexion and extension. Lateral and other motions can also affect the amount of telescoping, which accommodates, up to mechanically programmed joint limits, the natural dictates of the FSU motion. In a further embodiment, the center posts 7-1-4 and 8-1-4 (FIG. 22) keep the inferior and superior hydraulic cylinders from separating at maximum extension, thus preserving the mechanical linkage or inseparable connection between the vertebrae of the FSU. In a still further embodiment, the segmented walls have a mortise (5-1-2, 6-1-2, 7-1-2, 8-1-2) and tenon (5-1-3, 6-1-3, 7-1-3, 8-1-3) type bearing interface between adjacent outer walls 5-1-1 and 6-1-1 and adjacent inner walls 7-1-1 and 8-1-1 (FIG. 20). In an alternative embodiment, the segmented walls can have a lap joint bearing interface. Surface 5-2-2 laps 6-2-3 and 5-2-3 laps 6-2-2 on the outer segmented walls 5-2-1 and 6-2-1 (FIG. 23) while 7-2-2 laps 8-2-3 and 7-2-3 laps 8-2-2 on the inner segmented walls 7-2-1 and 8-2-1 (FIG. 24). The scope of the invention is not limited to these two types of joints between the segmented walls. One skilled in the art can devise many other types of joints for the sliding walls of the subject invention. Such variations are contemplated to be within the scope of the subject invention.

In a further embodiment of the subject invention, hydraulic portals 9-1-2 (FIG. 21) and 11-1-4 (FIG. 4 and FIG. 25) through the bottom of base ring 9-1 and top cap 11-1 of the central hydraulic cylinder allow transfer of fluid into and out of the telescoping cylinders. The hydraulic fluid, which can be pumped under pressure by the natural action of spinal flexion and extension, tends to separate all the interacting bearing surfaces in a manner similar to the action of synovial fluid in a healthy joint; this can increase the efficiency of the bearing surface and reduce wear. Such fluids can include, but are not limited to, a biocompatible silicone fluid, a biocompatible saline solution, oils of various types and viscosities, water, gels, other viscous materials, or combinations thereof.

Figure 2A:
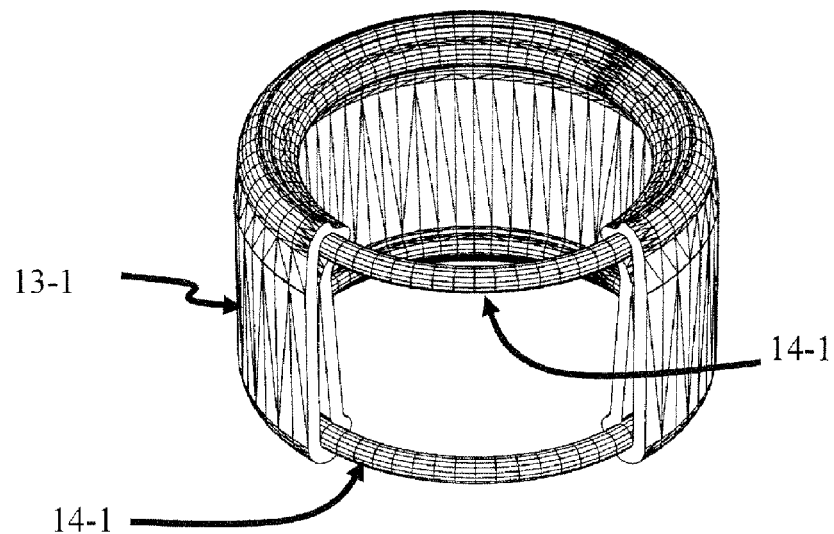
FIG. 2A illustrates an embodiment of a boot of the subject invention utilizing a double-layered, resilient, fiber-reinforced elastomer matrix (13-1) that can be firmly attached to the superior and inferior vertebral plates (12-1 and 1-1). Clamping and reinforcing rings embed into the boot matrix (14-1). Various fiber weaving schemes can use the rings as a starting platform for the weave. Cushioning elements, or different types of compressible and non-compressible fluids, can be placed between the two layers of the boot.
Figure 2B:
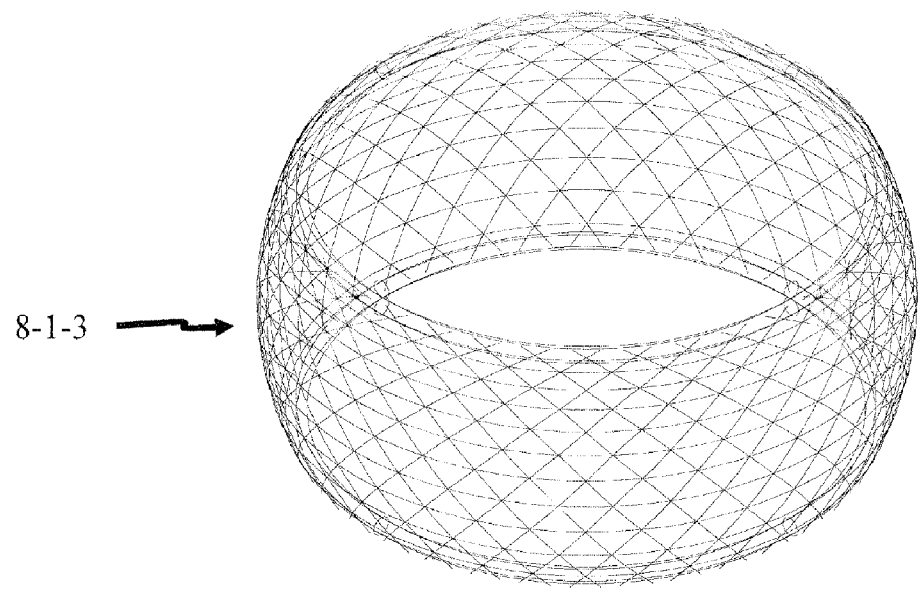
FIG. 2B illustrates an alternative embodiment of a boot of the subject invention having a spherical cross weave 8-1-3.
Figure 3:
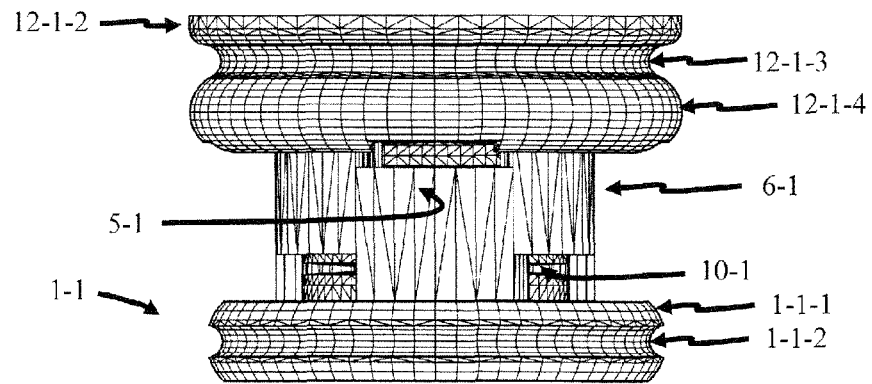
FIG. 3 illustrates an embodiment of the invention without the boot, revealing the inferior segmented-wall portion of the hydraulic cylinder (5-1) and the superior segmented-wall portion of the hydraulic cylinder (6-1). These walls slide with respect to each other along the axis of the cylinder as the vertebral plate 12-1 displaces with respect to 1-1 along that axis. The clamping rings 14-1 within the boot clamp onto 1-1 by means of groove 1-1-2 and onto 12-1 by means of groove 12-1-3. Wall gaps, which can serve as fluid portals, reveal the central spring elements 10-1 as the wall segments slide in extension.
Figure 4:
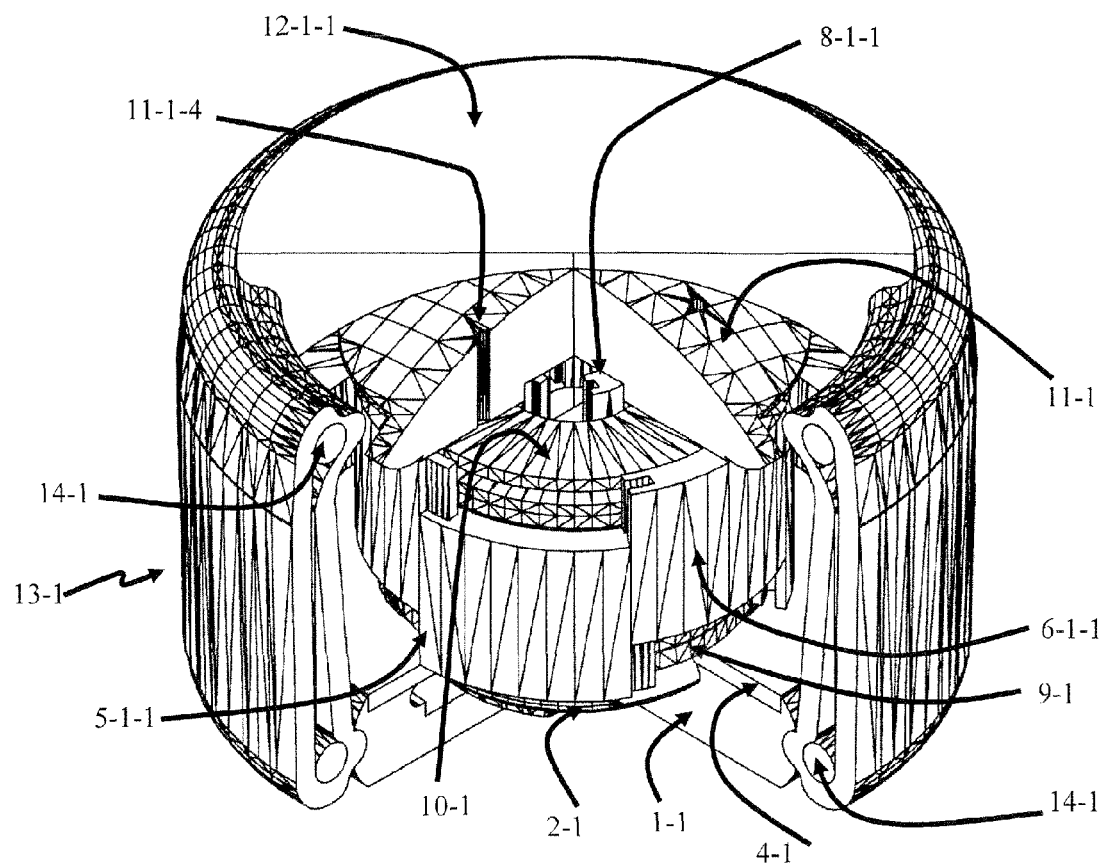
FIG. 4 reveals, in a perspective quadrant-cutaway view, the principal elements of an embodiment of the assembled invention.

The subject invention provides a spinal disc prosthesis, as shown, for example, in FIG. 1, FIG. 4, FIG. 11, FIG. 32 FIG. 33, and FIG. 34 that is capable of providing spatial movement with up to 6 independent degrees of freedom. The modular prosthetic disc of the subject invention contains the mechanisms responsible for its general motion capability. In a further embodiment, the prosthesis can be surrounded by an impermeable boot 13-1 formed of a resilient, fiber-reinforced elastomer matrix that firmly attaches to the superior and inferior vertebral plates 12-1 and 1-1. In a particular embodiment, the boot fiber weave is diamond shaped and can be woven into cylindrical (FIG. 13) or spherical crossweave form, seen for example in FIG. 2B) or in bellows form shown, for example in U.S. Pat. No. 7,361,192 (Doty), previously incorporated herein by reference. Various types of reinforcing materials, weave type, and the fiber properties, including mixed fibers can be used to construct a boot of the subject invention, similar to techniques and compositions utilized in manufacturing automobile tires. The boot structures can further have reinforcing rings 14-1 at or about either end, as illustrated for example, in FIG. 2A and FIG. 4. These rings with surrounding fiber and elastomer can be attached fixedly to 12-1 and 1-1 by any of a variety of methods known to a person with skill in the art. In a particular embodiment, grooves 12-1-3 and 1-1-2 can be configured for the rings to clamp tightly onto the lateral surfaces of 12-1 and 1-1 so the boot can withstand large forces without tearing the boot matrix or pulling the boot away from the device. In a further embodiment, the boot can enclose upon itself into a double-layered cylindrical tube around the clamping rings. A toroidal belt 19-1, in a further embodiment can be partially interwoven into the boot weave matrix to provide additional cushioning and strength. The boot can also form a seal to block out bio-debris that might reduce joint mobility or the leaking of internal fluid or cushion elements from inside the boot volume.

In a specific embodiment, principal mechanisms of the subject invention include a multi-curvate ball-and-socket joint for general orienting in three-dimensional space of the superior vertebra of an FSU with respect to its inferior vertebra and a slider joint central hydraulic cylinder, together with a planar bearing, for general positioning in three-dimensional space of the superior vertebra of an FSU with respect to its inferior vertebra, that establish an inseparable kinematic chain or kinematic linkage between a superior vertebral plate 12-1 (FIG. 28, FIG. 29, and FIG. 30) that fixedly attaches to the superior vertebra of an FSU and an inferior vertebral plate 1-1 (FIG. 12 and FIG. 13) that fixedly attaches to the inferior vertebra of the same FSU.

A spring element, in a one embodiment, is a series of one or more configured spring stacks (10-1). In a particular embodiment, up to 10 Belleville springs, are loosely fit (FIG. 20)

within the central hydraulic cylinder. In a particular embodiment, the Belleville springs are of a bio-inert material. Other embodiments can configure combinations of series and parallel stacks with varying spring constants to provide non-linear spring performance when the springs are allowed to saturate, i.e. reach their maximum allowed deflection and, thus, operate the stack out of its linear range. For example, as Belleville springs with smaller spring constants reach maximum deflection, the overall spring constant will increase.

Figure 11:
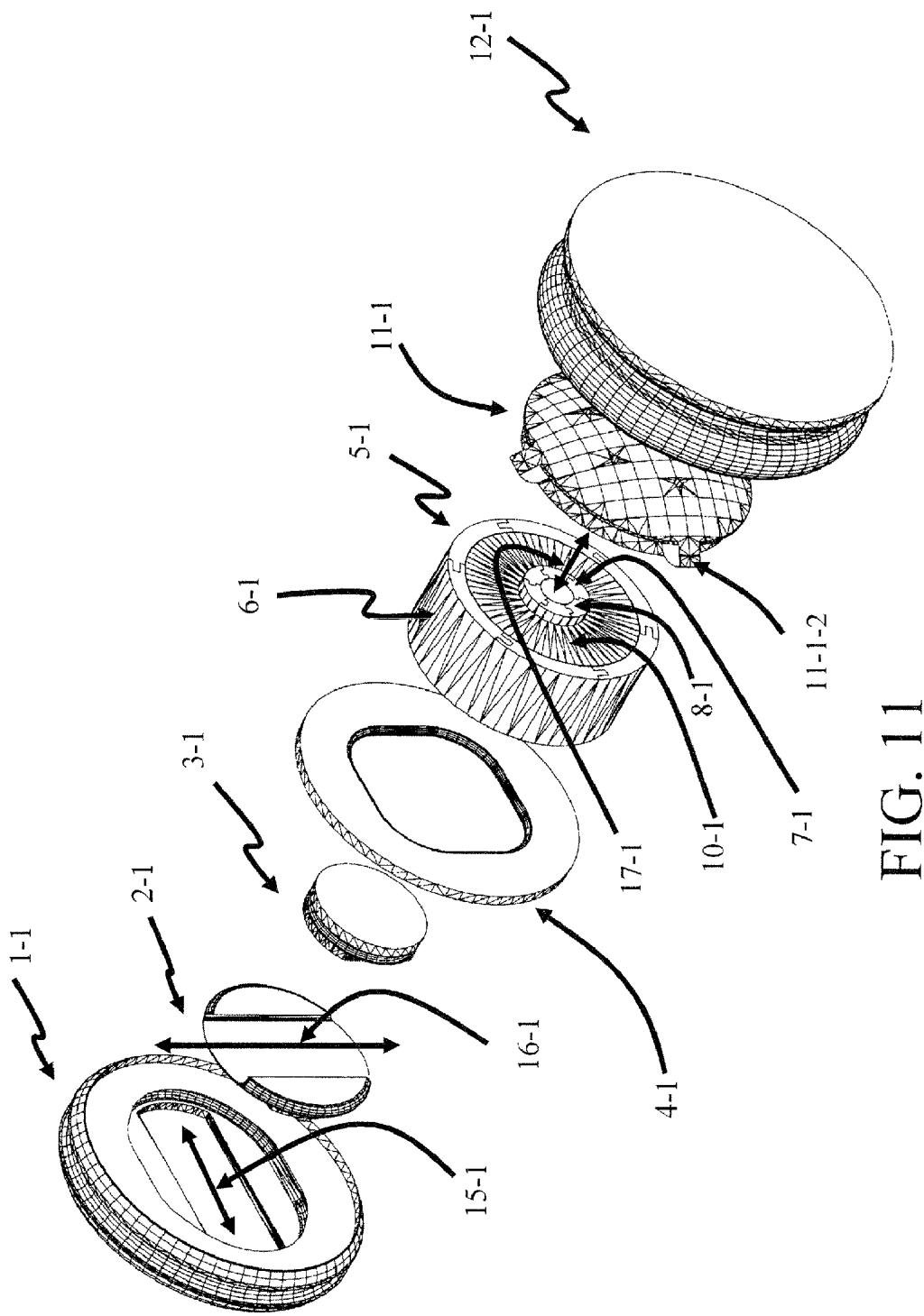
FIG. 11 shows an exploded perspective of an embodiment of the subject invention without the boot, illustrating several of the invention elements, from left to right, the sagittal prismatic axis 15-1 within the inferior vertebral plate 1-1, the sagittal-lateral plane bearing platform 2-1 with a lateral prismatic raceway on its top surface and joint axis 16-1, the lateral bearing platform 3-1, the planar bearing lock ring 4-1, the inferior hydraulic cylinder outer walls 5-1, the superior hydraulic cylinder outer walls 6-1, the inferior core hydraulic cylinder 7-1, the superior core hydraulic cylinder 8-1, the spring stack element 10-1, the multi-curvate "ball" 11-1 with axial rotation joint stop elements 11-2, and the superior vertebral plate 12-1. Not seen in this figure is the inferior hydraulic cylinder wall support ring 9-1.
Figure 26:
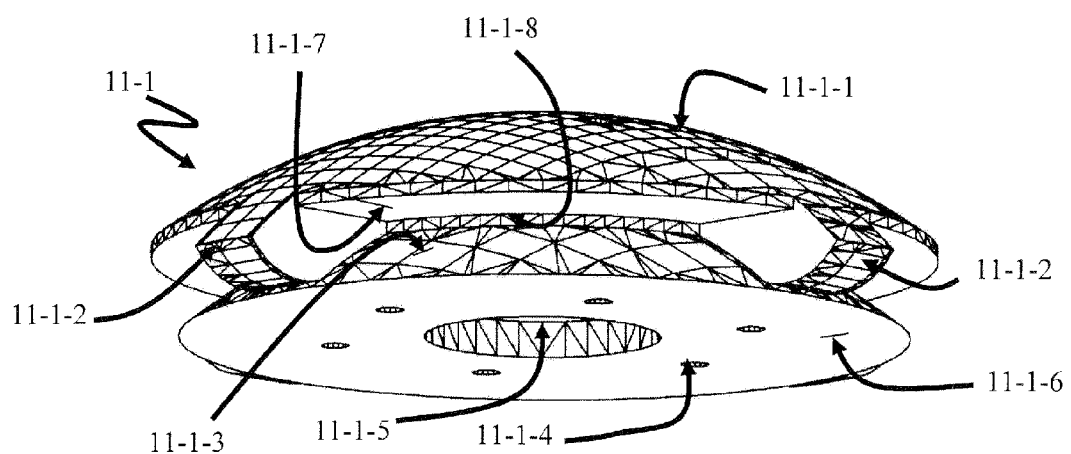
FIG. 26 shows more of the structure of an embodiment of element 11-1. In this embodiment, the undersurface of 11-1-6 serves as the top to the central hydraulic cylinder whose superior segmented outer walls fixedly attach to it. Further, the cavity 11-1-5 encompasses the cranial ends of the inferior and superior inner core segmented walls. The superior inner core segmented walls 8-1-1 (8-2-1) fixedly attach to the upper surface and sides of the cavity 11-1-5 (refer to FIG. 31) while the segmented walls 7-1-1 freely slide in and out of the cavity 11-1-5. The cavity 11-1-8 allows for the insertion of a conforming piece on the superior vertebral plate 12-1 that rotationally locks 11-1 and 12-1 together for allowable "ball-and-socket" rotations of 12-1 on surfaces 11-1-1 and 11-1-3.

In a further embodiment, the segmented-walls 7-1-1 and 8-1-1 of inner cores 7-1 and 8-1 (FIG. 11 and FIG. 22) loosely fit into inner circular opening of the springs, allowing the cores to slide by the springs during operation while providing an intact central shaft to stabilize and secure the spring elements. In this embodiment, the segmented walls slide past one another without hindrance, and, at full compression, mesh as shown in FIG. 11. The top exposed portions of 7-1 and 8-1, at full compression, can fit into a cavity 11-5 in the under surface 11-1-6 of element 11-1 (FIG. 26).

Figure 38:
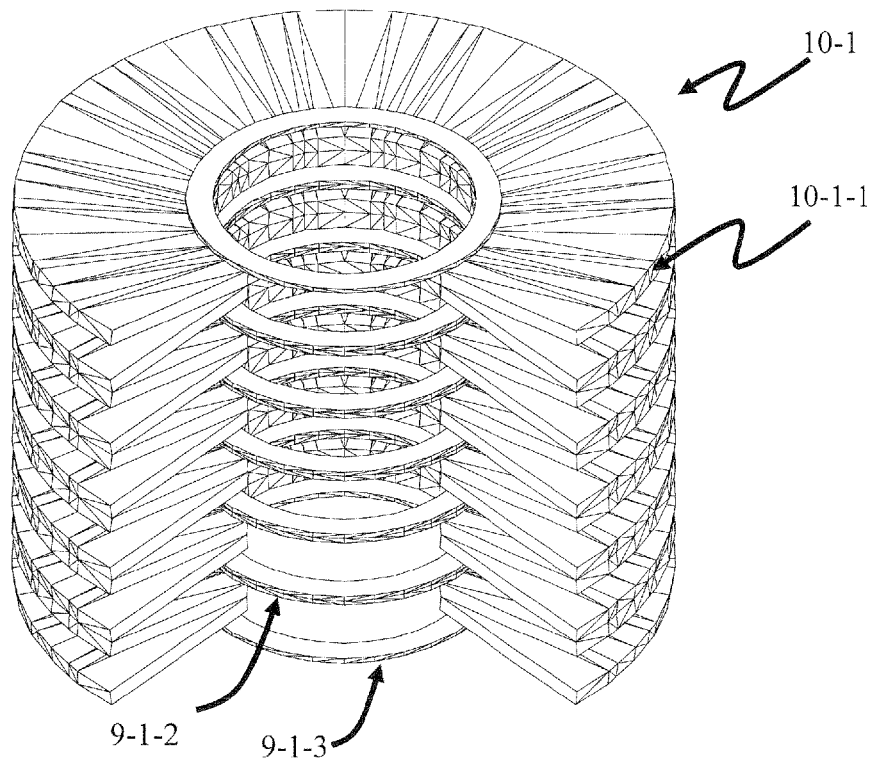
FIG. 38 shows one embodiment of the spring stack 10-1 using Belleville springs 10-1-1 in a series stack with guard rings 9-1-2 and 9-1-3. The guard rings keep series of approximately matched-pairs of Belleville springs from inverting to parallel configuration under full compression.
Figure 39:
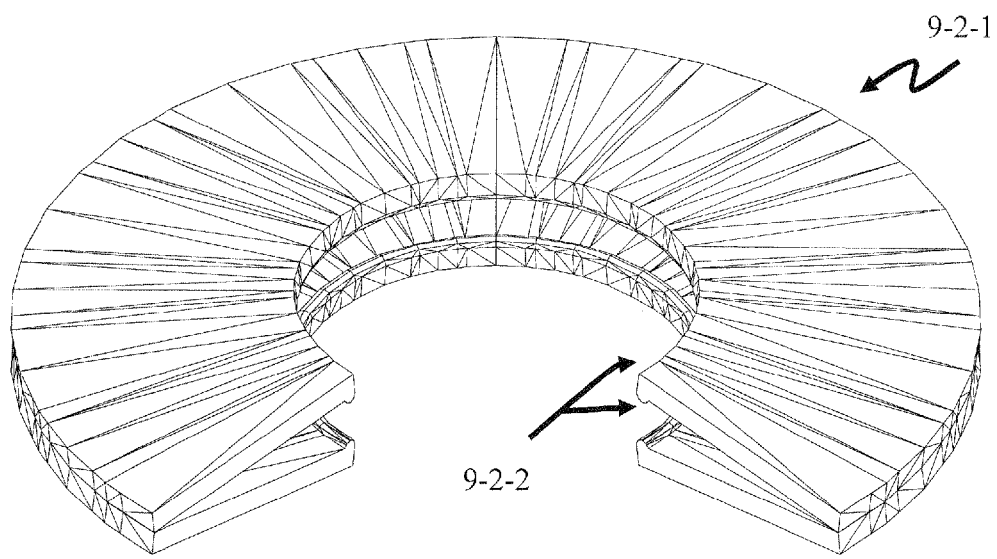
FIG. 39 demonstrates another embodiment of the subject invention utilizing a modified Belleville spring 9-2-1 comprising raised lips 9-2-2 on the edge shown. In this embodiment, when series spring configurations use approximately matched-pairs, the edges prevent complete closure under full compression and, hence, prevent inversion of a washer in the pair.

In one embodiment, the outer walls 5-1 and 6-1 of the hydraulic cylinder have conforming curvate shapes, which can also help stabilize the spring stack. In a further embodiment, seen for example, in FIGS. 20 and 21, the outer wall curvate shape is cylindrical. In a still further embodiment, sufficient space is provided between 5-1 and 6-1, and the springs to allow them to be compressed as much as 100%. But, in one alternative embodiment, guard slip-rings 9-1-2 and 9-1-3 (FIG. 38) or, in another alternative embodiment, integrated lip guards 9-2-2 (FIG. 39) are included to prevent inversion of one or more Belleville springs in the stack, i.e., the frustum of the spring changing from pointing up to down or down to up. In one embodiment, a guard slip-ring is approximately ¼ to approximately ½ the height of a single Belleville spring. In the alternative embodiment, the lip guards are approximately ¼ the height of a Belleville spring. Usually, either lip guards or the guard slip-rings are necessary, but both could be utilized if necessary. The advantage of the guard slip-rings is that standard Belleville springs can be used in the spring stack. The advantage of the lip guards is that a separate part is not needed to eliminate spring inversion.

A person with skill in the art would recognize that an inversion of any spring can damage the spring and can change, at least minimally, the spring constant of the stack by converting a series configuration, in which the inverted spring is a part, into a parallel configuration. Unless the spring re-inverts, this can have a deleterious effect on the intended operation of the device and should be avoided. Similarly, a parallel configuration would convert to a series configuration if only one spring inverted. Guard slip rings or lip guards can, thus, restrict the amount of linear displacement along the axial axis since the springs are prevented from closing down completely.

In one embodiment, the guard slip rings lie in the active displacement space of the spring(s) and do not require a ring stub between stacked springs. This reduces the height for the spring stack, a critical aspect since the space height available is limited. The method taught here also provides that the Belleville springs themselves can be modified with lip guards that perform the same function as the guard slip-rings, without requiring a separate device. The use of deflection-limiting guards can prevent the inversion singularity that occurs for Belleville springs if 100% deflections are allowed. If series coupled springs are not matched in pairs, there is some risk of spring inversion. For instance, if one spring in series with another has a much smaller spring constant than the second spring in the pair, the softer spring might invert before the stiffer spring compresses any significant amount. To avoid this possibility, approximately-matched series coupled Belleville springs can be desirable.

For 10 springs in series, the total displacement equals $10 \cdot h_e$ millimeters, where $h_e$, in millimeters, is the effective height of the Belleville spring, i.e., the actual amount the guards will allow each spring to compress. For example, if $h_e$ equals 0.224 mm, the spring stack of 10 springs in series will compress a maximum of 2.24 mm. Therefore, a Belleville spring with height 0.32 mm and guard lips of 0.08 mm will constrain a spring in a serial matched pair to compress no more than 70% of its height. The effective height then is 0.7 times 0.32 mm or 0.224 mm. At maximum compression, the central hydraulic cylinder and spring stack essentially becomes a fixed column between the FSU vertebrae that transmits any further compression forces to the FSU below.

In one embodiment, the multi-spherical surface "ball" 11-1 will limit axial rotations by means of one or more stops 11-1-2. In a specific embodiment, axial rotation of the multi-spherical ball is limited by four stops 11-1-2. Compound lateral and sagittal rotations can be limited by the interaction of edge 12-1-5 (FIG. 29, FIG. 30, FIG. 31) with the cavity 11-1-8 whose surfaces 11-1-7 and 11-1-3 conform with corresponding surfaces of projections 12-1-5, as that projection slides and fits into the cavity 11-1-8 as 12-1 rotates about 11-1. The deeper cavity 11-1-8 is with respect to projections 12-1-5, then the greater the angle of rotation possible about a given axis through the common center of spherical surfaces 11-1-1 and 11-1-3. Thus, in this embodiment, control of the cavity depth 11-1-8 and/or the extent of the projections 12-1-5 can allow mechanically programming lateral and sagittal angle joint stops. In a further embodiment, pure axial rotations with the superior vertebral cap 12-1 centered on the "ball" 11-1 can be mechanically programmed with joint stops 11-1-2. In one embodiment, the maximum angle of rotation about an axis parallel to the sagittal axis and passing through the rotation center can be 15 degrees. The maximum angle of rotation about an axis parallel to the lateral axis and passing through the rotation center can be 15 degrees. The maximum angle of rotation about an axis parallel to the axial axis and passing through the rotation center can be 15 degrees.

Hydraulic portals 11-1-4 can allow passage of lubricating fluid to the joint surface 11-1-1 and thence, by drainage, to 11-1-3. In one embodiment, hydraulic channels can also lead to surfaces 11-1-3 as well (not shown).

Figure 31:
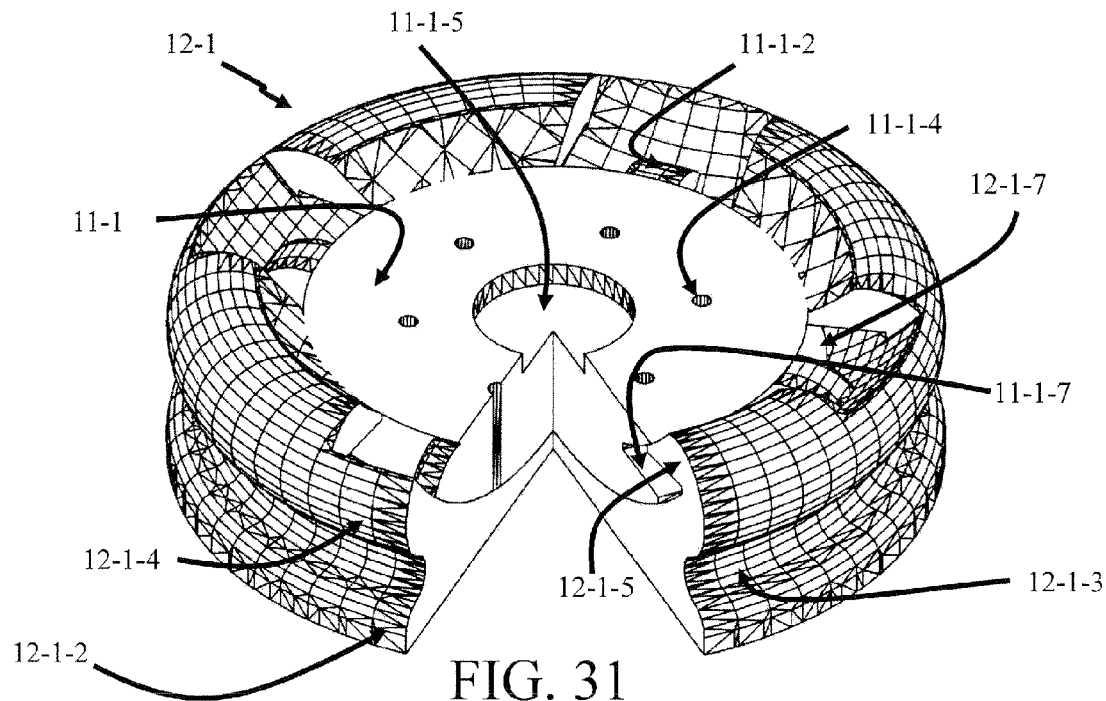
FIG. 31 illustrates an embodiment of a multi-curvate ball that fits into an embodiment of a multi-curvate cavity when the curvate surfaces are spherical.
Figure 32:
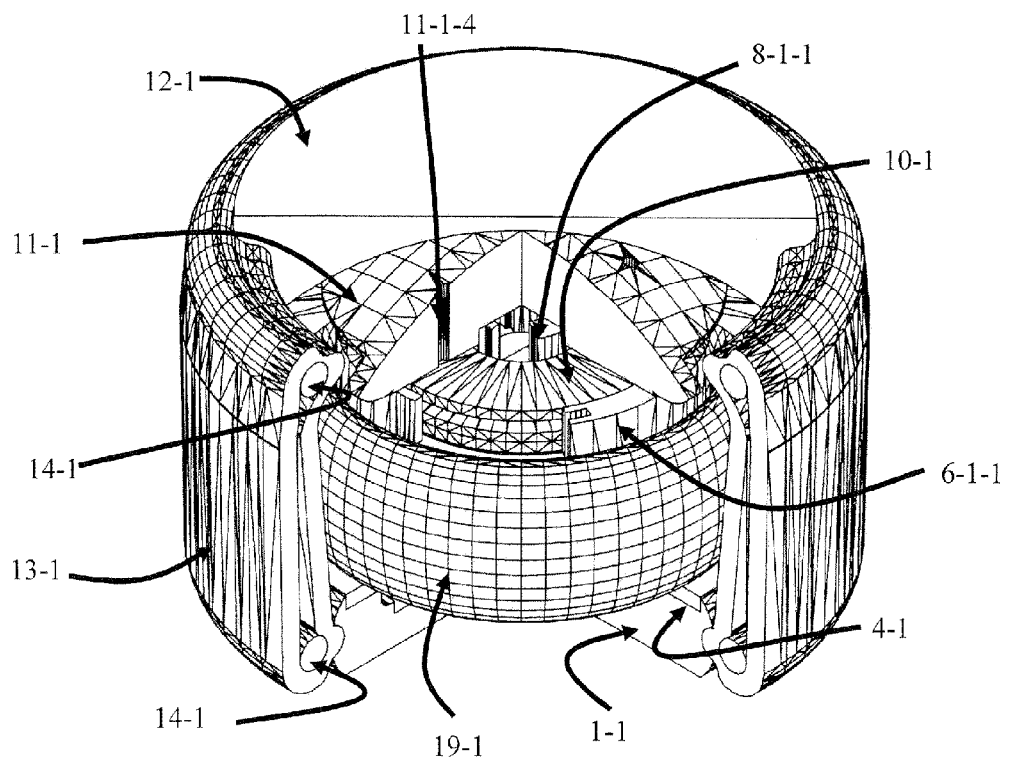
FIG. 32 shows a quadrant cutaway of an embodiment of the subject invention with the toroidal belt 19-1 installed around the central hydraulic cylinder.

The superior vertebral plate 12-1 receiving cavity 12-1-10 curvate surface 12-1-6 conforms to upper curvate surface 11-1-1, said surfaces being spherical in a particular embodiment. Stop gap 12-1-7 allows for joint stop element 11-1-2 therein to rotate about the center of rotation without hindrance within a specific range of rotations. Outside the rotation range about any particular axis of rotation, 11-1-2 will interfere with end surfaces of features 12-1-5 and impede further rotation. A perspective, underneath view of the "ball" 11-1 fitted into the cavity of 12-1-6 of the superior vertebral plate 12-1 illustrates one example of how the elements conform to each other (FIG. 31).

In various embodiments, top 12-1-1 of the superior vertebral plate 12-1 (FIG. 28) can be configured by those skilled in the art to allow the superior vertebral plate to fuse with a superior vertebra in an FSU, for example, by the use of titanium screws, projecting teeth elements and the like. The grove 12-1-3 can provide a means for fixing a boot clamping ring to the plate. Smooth, curvate surfaces 12-1-2 and 12-1-4 eliminate cutting edges and allow the boot to slide over them without damage.

Figure 33:
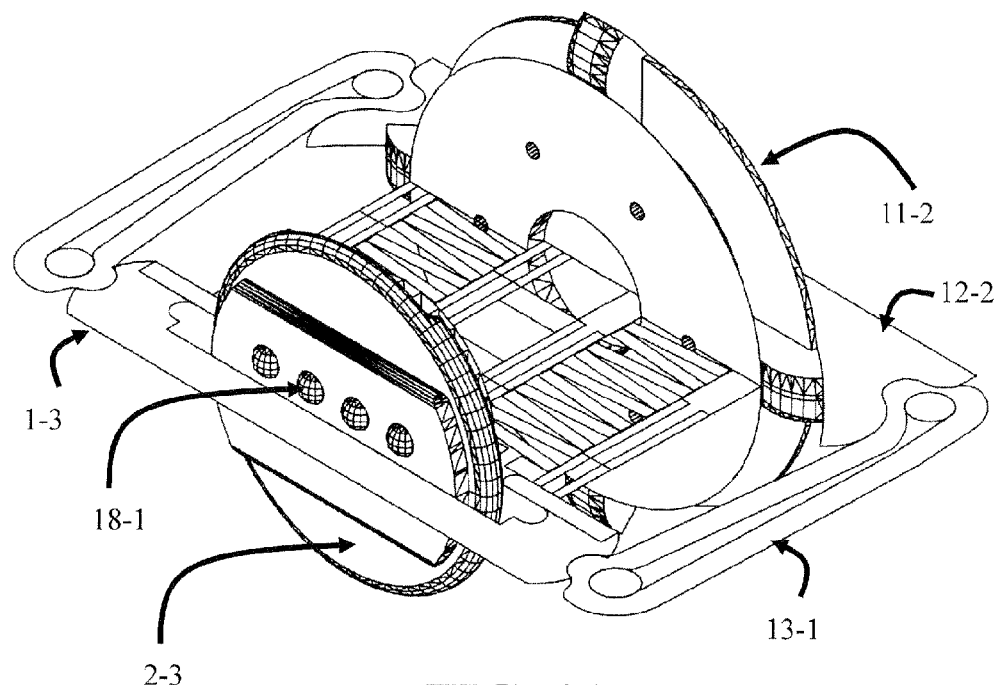
FIG. 33 and FIG. 34 illustrate how higher order pairs for the multi-curvate ball joint and the planar joint can be created, for example, by incorporating ball bearings 18-1. For clarity, portions of the device are shown in sectional view. In order to incorporate higher order bearings, the elements 1-3, 2-3, 3-3, 11-2 and 12-2 can differ from the corresponding elements of the previous embodiment, namely, 1-1, 2-1, 3-1, 11-1 and 12-1. Similarly, high order pairs can be used for planar bearing elements 1-2, 2-2, and 3-2.
Figure 34:
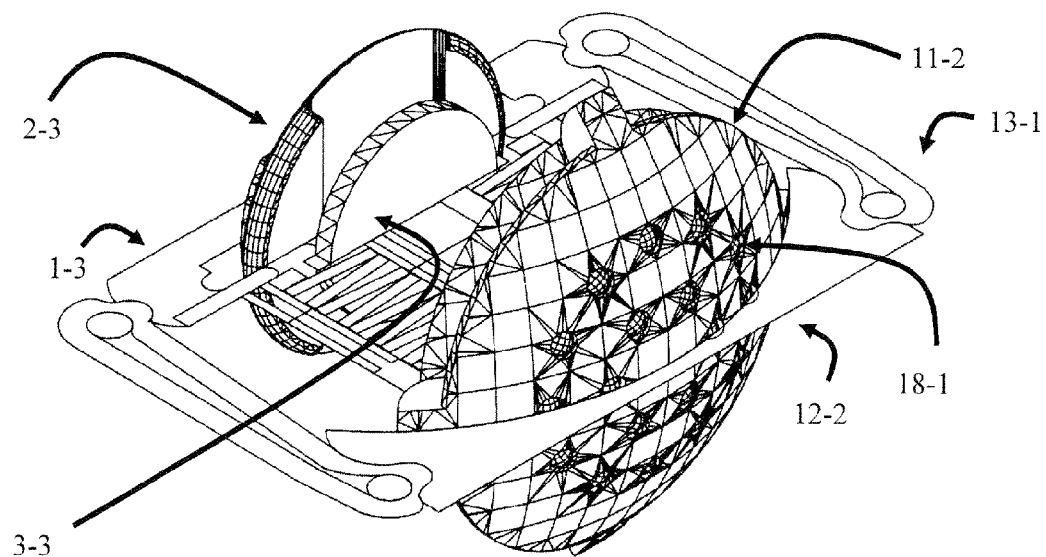

The low level pair joints of the subject invention can also be replaced by a variety higher order pairs by utilizing ball, rod, cylindrical and other types of bearings. Illustrations of non-limiting examples of ball bearings 18-1 in the sagittal prismatic joint 2-3 and the ball element spherical surface 11-2 are shown in FIG. 33 and FIG. 34. The lateral prismatic joint between 2-3 and 3-3 can also be a higher order pair (bearings not shown). Elements 1-3 and 12-2 may have structural differences to 1-1 and 12-1 due to the higher order pairs 2-3, 3-3, and 11-2, namely, clearances for bearings. Another embodiment can use higher order pairs for the planar joint in FIG. 19. Anyone skilled in the art can effect these modifications without too much difficulty.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

It should be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

I claim:

1. A prosthetic device comprising:
a superior vertebral plate;
a ball element having an upper spherical surface and an undersurface, wherein the upper spherical surface is moveably secured within and, at least partially, conforms to a receiving cavity within the superior vertebral plate,
a central cylinder comprising,
a superior external segmented wall fixedly attached at one end to the undersurface of the ball element; and
an inferior external segmented wall slidably engaged with the superior external segmented wall and fixedly attached at one end to a base ring, wherein the base ring comprises a central opening;
an inner cylinder core within the central cylinder comprising,
a superior inner segmented wall fixedly attached at or near a first end to the undersurface of the ball element;
a first center post element fixedly attached at or near a second end of the superior inner segmented wall;
an inferior inner segmented wall slidably engaged with the superior inner segmented wall and fixedly attached, at or near a first end, to a means for providing at least one degree of translational motion, wherein the means for providing at least one degree of translational motion is fixedly attached within the central opening of the base ring;
a second center post element fixedly attached at or near a second end of the inferior inner segmented wall, between the first center post element and the undersurface of the ball element, such that the first and second center post elements inhibit the walls of the central cylinder and the inner cylinder core from separating; and
an inferior vertebral plate slidably connected to the means for providing at least one degree of translational motion,
such that when said device is implanted in a spine with the superior and inferior vertebral plates engaged with a first and second vertebra, said device forms a kinematic chain of connected, inseparable, articulating components between said first and second vertebra, wherein said device has means for providing at least one and up to three independent rotational degrees of freedom and additional means for providing at least one and up to three independent linear degrees of freedom.

2. The device, according to claim 1, further comprising a boot fixedly engaged with the superior vertebral plate and the inferior vertebral plate, such that the means for providing the degrees of freedom are sealed within by the boot thereby inhibiting materials external to said device from contacting moveable elements of the device.

3. The device, according to claim 2, wherein the boot comprises a strong, flexible, non-homogeneous, fiber reinforced elastomer matrix.

4. The device, according to claim 3, wherein the boot is capable of providing torsional load bearing.

5. The device, according to claim 4, wherein the boot is capable of providing non-linear compression and extension.

6. The device, according to claim 3, further comprising a toroidal tube at least partially surrounding the central cylinder.

7. The device, according to claim 6, wherein the toroidal tube is an elastomer.

8. The device, according to claim 6, wherein the toroidal tube is fixedly attached to the superior plate and the inferior plate.

9. The device, according to claim 6, wherein the toroidal tube is at least partially interwoven into the boot matrix.

10. The device, according to claim 2, further comprising a biocompatible lubricant sealed within by the boot.

11. The device, according to claim 10, further comprising one or more hydraulic portals that assist in distributing the biocompatible lubricant.

12. The device, according to claim 11, wherein distribution of the biocompatible lubricant by the hydraulic portals provides shock absorbing characteristics.

13. The device, according to claim 2, wherein the boot is a double-walled tubular structure.

14. The device, according to claim 13, further comprising one or more clamping rings.

15. The device, according to claim 14, wherein the superior vertebral plate and the inferior vertebral plate further comprise one or more grooves for receiving the one or more clamping rings.

16. The device, according to claim 14, wherein the boot is formed around the one or more clamping rings.

17. The device, according to claim 16, further comprising one or more cushioning elements within the tubular structure.

18. The device, according to claim 17, wherein the one or more cushioning elements is an elastomer.

19. The device, according to claim 1, wherein the means for providing at least one degree of translational motion is slidably secured to the inferior vertebral plate utilizing a planar bearing cap lock.

20. The device, according to claim 1, wherein the segmented walls of the central cylinder and the segmented walls of the inner cylinder core are slidably engaged utilizing one or more mortise and tenon joints, lap joints, or combinations thereof.

21. The device, according to claim 20, wherein the central cylinder comprises three superior external segmented walls and three inferior external segmented walls.

22. The device, according to claim 21, wherein the inner cylinder core comprises three superior inner segmented walls and three inferior inner segmented walls.

23. The device, according to claim 22, further comprising one or more cushioning elements on the first center post element.

24. The device, according to claim 22, further comprising one or more cushioning elements on the second center post element.

25. The device, according to claim 22, wherein the segmented walls of the central cylinder and the segmented walls of the inner cylinder core are slidably engaged utilizing one or more mortise and tenon joints, lap joints, or combinations thereof.

26. The device, according to claim 25, further comprising one or more cushioning elements between one or more of the articulating components.

27. The device, according to claim 1, wherein the ball element further comprises one or more rotational joint stop elements to control rotation relative to the superior vertebral plate.

28. The device, according to claim 27, wherein the superior vertebral plate comprises one or more stop gaps for limiting the rotation of the joint stop elements.

29. The device, according to claim 28, wherein the ball element is moveably secured within the superior vertebral plate utilizing multiple spherical surfaces interacting with one or more corresponding surfaces on the superior vertebral plate.

30. The device, according to claim 29, wherein two spherical surfaces having a common center but different radii of curvature are utilized to moveably secure the ball element within the superior vertebral plate.

31. The device, according to claim 27, wherein the one or more rotational joint stop elements further comprise one or more cushioning elements.

32. The device, according to claim 1, further comprising one or more joint stops for limiting one or more linear degrees of freedom.

33. The device, according to claim 32, wherein the joint stops further comprise one or more cushioning elements.

34. The device, according to claim 1, further comprising one or more bearings between one or more joint surfaces or sliding surfaces.

35. The device, according to claim 1, wherein the means for providing at least one degree of translational motion comprises a planar bearing assembly.

36. The device, according to claim 35, wherein the planar bearing assembly comprises:
a planar bearing platform having one or more surfaces on a first side and a lateral raceway on a second side wherein the one or more surfaces on the first side are slidably connected to the inferior vertebral plate; and
a lateral bearing platform wherein the inferior inner segmented wall is fixedly attached to a first side and having a second side with one more surfaces that operably engage and slide within the lateral raceway.

37. The device, according to claim 1, further comprising one or more spring elements positioned between the central cylinder and the inner cylinder core.

38. The device, according to claim 37, wherein the one or more spring elements comprise one or more Belleville springs.

39. The device, according to claim 37, further comprising one or more cushioning elements between the central cylinder and the inner cylinder core.

40. A prosthetic device comprising:
a superior vertebral plate;
a ball element having an upper spherical surface and an undersurface, wherein the upper spherical surface is moveably secured within and, at least partially, conforms to a receiving cavity within the superior vertebral plate,
a central cylinder comprising,
a superior external segmented wall fixedly attached at one end to the undersurface of the ball element; and
an inferior external segmented wall slidably engaged with the superior external segmented wall and fixedly attached at one end to a base ring, wherein the base ring comprises a central opening;
an inner cylinder core comprising,
a superior inner segmented wall fixedly attached at or near a first end to the undersurface of the ball element;
a first center post element fixedly attached at or near a second end of the superior inner segmented wall;
an inferior inner segmented wall slidably engaged with the superior inner segmented wall and fixedly attached, at or near a first end, to a lateral bearing platform of a planar hearing assembly, wherein the lateral bearing platform is fixedly attached within the central opening of the base ring;
a second center post element fixedly attached at or near a second end of the inferior inner segmented wall, between the first center post element and the undersurface of the ball element, such that the first and second center post elements inhibit the walls of the central cylinder and the inner cylinder core from separating; and
an inferior vertebral plate operably connected to a planar bearing platform of the planar bearing assembly,
such that when said device is implanted in a spine with the superior and inferior vertebral plates engaged with a first and second vertebra, said device forms a kinematic chain of connected, inseparable, articulating components between said first and second vertebra, wherein said device has means for providing at least one and up to three independent rotational degrees of freedom and additional means for providing at least one and up to three independent linear degrees of freedom.

41. The device, according to claim 40, wherein the lateral bearing platform and the planar bearing platform of the planar bearing assembly are slidably connected.

42. The device, according to claim 41, wherein the slidable connection comprises a bearing surface on the lateral bearing platform positioned within a raceway of the planar bearing platform.

43. The device, according to claim 42, wherein the operable connection between the planar bearing platform and the inferior vertebral plate comprises a planar surface on the planar bearing platform slidably attached to a prismatic raceway in the inferior vertebral plate.

44. The device, according to claim 41, wherein the slidable connection between the lateral bearing platform and the planar bearing platform and the operable connection between the planar bearing platform and the inferior vertebral plate provide up to two orthogonal, translational degrees of freedom.

45. The device, according to claim 44, further comprising one or more cushioning elements between one or more of the articulating components.

46. The device, according to claim 40, wherein the planar bearing assembly is slidably secured to the inferior vertebral plate utilizing a planar hearing cap lock.

47. The device, according to claim 40, further comprising one or more spring elements positioned between the central cylinder and the inner cylinder core.

48. The device, according to claim 47, wherein the one or more spring elements comprise one or more Belleville springs.

49. The device, according to claim 47, further comprising one or more cushioning elements between the central cylinder and the inner cylinder core.

50. The device, according to claim 40, further comprising a boot fixedly engaged with the superior vertebral plate and the inferior vertebral plate, such that the means for providing the degrees of freedom are sealed within by the boot, thereby preventing materials external to said device from contacting moveable elements of the device.

51. The device, according to claim 50, wherein the boot comprises a strong, flexible, non-homogeneous, fiber reinforced elastomer matrix.

52. The device, according to claim 51, wherein the boot is capable of providing torsional load bearing.

53. The device, according to claim 52, wherein the boot is capable of providing non-linear compression and extension.

54. The device, according to claim 50, further comprising a biocompatible lubricant sealed within by the boot.

55. The device, according to claim 54, further comprising one or more hydraulic portals that assist in distributing the biocompatible lubricant.

56. The device, according to claim 55, wherein distribution of the biocompatible lubricant by the hydraulic portals provides shock absorbing characteristics.

57. The device, according to claim 50, wherein the boot is a double-walled tubular structure.

58. The device, according to claim 57, further comprising one or more clamping rings.

59. The device, according to claim 58, wherein the boot is formed around the one or more clamping rings.

60. The device, according to claim 59, further comprising one or more cushioning elements within the double-walled tubular structure.

61. The device, according to claim 58, wherein the superior vertebral plate and the inferior vertebral plate further comprise one or more grooves for receiving the one or more clamping rings.

62. The device, according to claim 40, wherein the segmented walls of the central cylinder and the segmented walls of the inner cylinder core are slidably engaged utilizing one or more mortise and tenon joints, lap joints, or combinations thereof.

63. The device, according to claim 62, further comprising one or more cushioning elements on the first center post element.

64. The device, according to claim 62, further comprising one or more cushioning elements on the second center post element.

65. The device, according to claim 40, further comprising a toroidal belt at least partially surrounding the central cylinder.

66. The device, according to claim 40, wherein the ball element further comprises one or more rotational joint stop elements to control rotation relative to the superior vertebral plate.

67. The device, according to claim 66, wherein the rotational joint stop elements further comprise one or more cushioning elements.

68. The device, according to claim 66, wherein the superior vertebral plate comprises one or more stop gaps for limiting the rotation of the rotational joint stop elements.

69. The device, according to claim 68, wherein the ball element is moveably secured within the superior vertebral plate utilizing multiple spherical surfaces interacting with one or more corresponding surfaces on the superior vertebral plate.

70. The device, according to claim 69, wherein two spherical surfaces having a common center but different radii of curvature are utilized to moveably secure the ball element within the superior vertebral plate.

71. The device, according to claim 40, further comprising one or more joint stops for limiting one or more linear degrees of freedom.

72. The device, according to claim 71, wherein the joint stops further comprise one or more cushioning elements.

73. The device, according to claim 40, further comprising one or more bearings between one or more joint surfaces or sliding surfaces.

74. A method for approximating spinal disc movement comprising:
   implanting within a spine of a patient a prosthetic device comprising;
   a superior vertebral plate;
   a ball element having an upper spherical surface and an undersurface, wherein the upper spherical surface is moveably secured within and, at least partially, conforms to a receiving cavity within the superior vertebral plate,
   a central cylinder comprising,
      a superior external segmented wall fixedly attached at one end to the undersurface of the ball element; and
      an inferior external segmented wall slidably engaged with the superior external segmented wall and fixedly attached at one end to a base ring, wherein the base ring comprises a central opening;
   an inner cylinder core within the central cylinder comprising,
      a superior inner segmented wall fixedly attached at or near a first end to the undersurface of the ball element;
      a first center post element fixedly attached at or near a second end of the superior inner segmented wall;
      an inferior inner segmented wall slidably engaged with the superior inner segmented wall and fixedly attached, at or near a first end, to a means for providing at least one degree of translational motion, wherein the means for providing at least one degree of translational motion is fixedly attached within the central opening of the base ring;
      a second center post element fixedly attached at or near a second end of the inferior inner segmented wall, between the first center post element and the undersurface of the ball element such that the first and second center post elements inhibit the walls of the central cylinder and the inner cylinder core from separating; and an inferior vertebral plate slidably connected to the means for providing at least one degree of translational motion, such that when said device is implanted in the spine with the superior and inferior vertebral plates engaged with a first and second vertebra, said device forms a kinematic chain of connected, inseparable, articulating components between said first and second vertebra, wherein said device has means for providing at least one and up to three independent rotational degrees of freedom and additional means for providing at least one and up to three independent linear degrees of freedom.

75. The method, according to claim 74, wherein the device is implanted within a patient with the superior vertebral plate more caudal than the inferior vertebral plate.

76. The method according to claim 74, further comprising one or more spring elements positioned between the central cylinder and the inner cylinder core.

77. The method, according to claim 76, wherein the spring elements comprise one or more Belleville springs.

78. The method, according to claim 76, further comprising one or more cushioning elements between the central cylinder and the inner cylinder core.

79. The method, according to claim 74, further comprising a boot fixedly engaged with the superior vertebral plate and the inferior vertebral plate, such that the means for providing the degrees of freedom are sealed within by the boot, thereby preventing materials external to said device from contacting moveable elements of the device.

80. The method, according to claim 79, wherein the boot comprises a strong, flexible, non-homogeneous, fiber reinforced elastomer matrix.

81. The method, according to claim 80, wherein the boot is capable of providing torsional load bearing.

82. The method, according to claim 81, wherein the boot is capable of providing non-linear compression and extension.

83. The method, according to claim 82, further comprising one or more quilt pads on the boot.

84. The method, according to claim 83, wherein the one or more quilt pads are filled with a cushioning material.

85. The method, according to claim 84, wherein the cushioning material is a fluid.

86. The method, according to claim 80, further comprising a toroidal tube at least partially surrounding the central cylinder.

87. The method, according to claim 86, wherein the toroidal tube is at least partially interwoven into the boot matrix.

88. The method, according to claim 79, further comprising a biocompatible lubricant sealed within the boot.

89. The method, according to claim 88, further comprising one or more hydraulic portals that assist in distributing the biocompatible lubricant.

90. The method, according to claim 89, wherein distribution of the biocompatible lubricant by the hydraulic portals provides shock absorbing characteristics.

91. The method, according to claim 79, wherein the boot is a double-walled tubular structure.

92. The method, according to claim 91, further comprising one or more clamping rings.

93. The method, according to claim 92, wherein the boot is formed around the one or more clamping rings.

94. The method, according to claim 93, further comprising one or more cushioning elements within the double-walled tubular structure.

95. The method, according to claim 94, wherein the one or more cushioning elements is a fluid.

96. The method, according to claim 95, wherein the fluid is compressible.

97. The method, according to claim 95, wherein the fluid is non-compressible.

98. The method, according to claim 92, wherein the superior vertebral plate and the inferior vertebral plate further comprise one or more grooves for receiving the one or more clamping rings.

99. The method, according to claim 74, wherein the means for providing at least one degree of translational motion is slidably secured to the inferior vertebral plate utilizing a planar bearing cap lock.

100. The method, according to claim 74, wherein the segmented walls of the central cylinder and the segmented walls of the inner cylinder core are slidably engaged utilizing one or more mortise and tenon joints, lap joints, or combinations thereof.

101. The method, according to claim 100, wherein the central cylinder comprises three superior external segmented walls and three inferior external segmented walls.

102. The method, according to claim 101, wherein the inner cylinder core comprises three superior inner segmented walls and three inferior inner segmented walls.

103. The method, according to claim 102, further comprising one or more cushioning elements on the first center post element.

104. The method, according to claim 102, further comprising one or more cushioning elements on the second center post element.

105. The method, according to claim 74, wherein the ball element further comprises one or more rotational joint stop elements to control rotation relative to the superior vertebral plate.

106. The method, according to claim 105, wherein the rotational joint stop elements further comprise one or more cushioning elements.

107. The method, according to claim 105, wherein the superior vertebral plate comprises one or more stop gaps for limiting the rotation of the rotational joint stop elements.

108. The method, according to claim 107, wherein the ball element is moveably secured within the superior vertebral plate utilizing multiple spherical surfaces interacting with one or more corresponding surfaces on the superior vertebral plate.

109. The method, according to claim 108, wherein two spherical surfaces having a common center, but different radii of curvature are utilized to moveably secure the ball element within the superior vertebral plate.

110. The method, according to claim 74, further comprising one or more joint stops for limiting one or more linear degrees of freedom.

111. The method, according to claim 110, wherein the joint stops further comprise one or more cushioning elements.

112. The method, according to claim 74, further comprising one or more bearings between one or more joint surfaces or sliding surfaces.

113. The method, according to claim 74, wherein the means for providing at least one degree of translational motion comprises a planar bearing assembly.

114. The method, according to claim 113, further comprising one or more cushioning elements between one or more of the articulating components.

* * * * *